US005989541A

United States Patent [19]
Iatrou

[11] Patent Number: 5,989,541
[45] Date of Patent: Nov. 23, 1999

[54] METHODS OF EXPRESSING PROTEINS IN INSECT CELLS AND METHODS OF KILLING INSECTS

[75] Inventor: Kostas Iatrou, Calgary, Canada

[73] Assignee: University Technologies International, Inc., Calgary, Canada

[21] Appl. No.: 08/931,830

[22] Filed: Sep. 16, 1997

Related U.S. Application Data

[62] Division of application No. 08/608,617, Mar. 1, 1996, Pat. No. 5,759,809, which is a continuation of application No. 08/172,653, Dec. 23, 1993, abandoned.

[51] Int. Cl.$^6$ .......................... A61K 48/00; C12N 15/86; C12N 15/67
[52] U.S. Cl. ...................... 424/93.2; 424/93.6; 435/69.1; 435/172.3; 435/320.1
[58] Field of Search ................................ 435/69.1, 172.1, 435/172.3, 320.1, 235.1, 348, 325; 424/93.2, 93.6

[56] References Cited

U.S. PATENT DOCUMENTS

| 4,745,051 | 5/1988 | Smith et al. | 435/69.51 |
|---|---|---|---|
| 5,004,687 | 4/1991 | Miller | 435/69.1 |
| 5,071,748 | 12/1991 | Miller | 435/69.1 |
| 5,077,214 | 12/1991 | Guarino et al. | 435/348 |
| 5,091,179 | 2/1992 | Biache et al. | 424/93.6 |
| 5,093,161 | 3/1992 | Hickle et al. | 424/93.461 |
| 5,093,120 | 3/1992 | Edwards et al. | 514/2 |
| 5,104,974 | 4/1992 | Sick et al. | 530/350 |
| 5,133,962 | 7/1992 | Sick et al. | 424/93.2 |
| 5,147,788 | 9/1992 | Page et al. | 435/69.1 |
| 5,155,037 | 10/1992 | Summers | 435/348 |
| 5,169,784 | 12/1992 | Summers et al. | 435/320.1 |
| 5,186,933 | 2/1993 | Estes | 424/215.1 |
| 5,194,376 | 3/1993 | Kang | 435/69.1 |
| 5,322,774 | 6/1994 | Peakman et al. | 435/69.1 |

FOREIGN PATENT DOCUMENTS

| 1 222 213 | 5/1987 | Canada . |
|---|---|---|
| 0 155 476 | 9/1985 | European Pat. Off. . |
| 0 505 207 | 9/1992 | European Pat. Off. . |
| 0 533 469 | 3/1993 | European Pat. Off. . |
| 0 542 466 | 5/1993 | European Pat. Off. . |
| 0 556 434 | 8/1993 | European Pat. Off. . |
| 0 568 178 | 11/1993 | European Pat. Off. . |
| WO 92/05265 | 4/1992 | WIPO . |
| WO 92/11363 | 7/1992 | WIPO . |
| WO 92/16619 | 10/1992 | WIPO . |
| WO 92/16637 | 10/1992 | WIPO . |
| WO 92/22654 | 12/1992 | WIPO . |
| WO 94/00585 | 1/1994 | WIPO . |

OTHER PUBLICATIONS

Blissard and Rohrmann (1990) "Baculovirus diversity and moleclar biology" *Ann. Rev. Entomol.*, 35:127–155.

Bradford (1976) "A rapid and sensitive method for the quantitation of microgram quantities of protein utilizing the principle of protein–dye binding" *Anal. Biochem.*, 72:248–254.

Carbonell et al. (1988) "Synthesis of a gene coding for an insect–specific scorpion neurotoxin and attempts to express it using baculovirus vectors," *Gene*, 73:409–418.

Carson et al., (1988) "Functional Mapping of an AcNPV Immediately Early Gene which Augments expression of the IE–1 trans–activated 39K Gene" *Virol.* 162:444–451.

Carson et al. (1991) "Transient expression of the *Autographa californica* nuclear polyhedrosis virus immediate–early gene, IE–N, is regulated by three viral elements" *J. Virol.* 65:945–951.

Cochran and Faulkner (1983) "Location of homologous DNA sequences interspersed at five regions in the baculovirus AcMNPV genome", *J. Virol.* 45:961–970.

Fotaki and Iatrou (1988) "Identification of a Transcriptionally Active Pseudogene in the Chorion Locus of the Silkmoth *Bombyx mori*," *J. Mol. Biol.*, 203:849–860.

Gorman et al. (1982) "Recombinant Genomes which express chloramphenicol acetyltransferase in mammalian cells," *Mol. Cell Biol.*, 2:1044–1051.

Goswami and Glazer (1991) "A simplified method for the production of recombinant baculovirus," *BioTechniques*, 10:626–630.

Grace (1967); "Establishment of a line of cells from the silkworm *Bombyx mori*," *Nature* 216:613.

Granados and Lawler (1981) "In vivo pathway of *Autographa californica* baculovirus invasion and infection," *Virol.*, 108:297–308.

Guarino and Dong (1991) "Expression of an enhancer–binding protein in insect cells transfected with the *Autographa californica* nuclear polyhedrosis virus IE–1 gene" *J. Virol.* 65:3676–3680.

Guarino et al., (1986) "Complete sequence and enhancer function of the homologous DNA regions of *Autographa californica* nuclear polyhedrosis virus" *J. Virol.* 60:224–229.

Guarino and Summers (1986) "Interspersed homologous DNA of *Autographa californica* nuclear polyhedrosis virus enhances delayed–early gene expression" *J. Virol.* 60:215–223.

(List continued on next page.)

*Primary Examiner*—David Guzo
*Attorney, Agent, or Firm*—Burns, Doane, Swecker & Mathis, L.L.P.

[57] ABSTRACT

Described herein is a method of expressing heterologous proteins in insect cells using an expression cassette comprising a structural gene for a heterologous protein physically attached to an insect cellular promoter and an enhancer. The cells may also express the IE-1 product. Also described herein is a method of killing insects comprising infecting the insects with a recombinant baculovirus comprising a structural gene for an incompatible protein functionally linked to an insect cellular promoter and an enhancer. The invention is also directed towards expression cassettes comprising an insect cellular promoter functionally linked to an enhancer wherein the promoter is capable of directing the expression of a heterologous protein in tissues containing the expression cassette, recombinant expression cassettes containing heterologous proteins, transplacement fragments, vectors and recombinant baculoviruses.

13 Claims, 13 Drawing Sheets

OTHER PUBLICATIONS

Guarino and Summers, (1987) "Nucleotide sequence and temporal expression of a baculovirus regulatory gene" *J. Virol.* 61:2091–2099.

Gubler and Hoffman (1983) "A simple and very efficient method of generating cDNA libraries," *Gene,* 25:263–269.

Gurevitz et al. (1991) "Nucleotide sequence and structure analysis of a cDNA encoding an alpha insect toxin from the scorpion *Leiurus quinquestriatus hebraeus*", *Toxicon* 29:1270–1272.

Hahnel and Schultz (1989) "Cloning and characterization of a cDNA encoding alkaline phosphatase in mouse embryonal carcinoma cells," *Clin, Chim. Acta,* 186:171–174.

Hanzlik et al. (1990) "Isolation and sequencing of cDNA clones coding for juvenile hormone esterase from *Heliothis virescens,*" *J. Biol. Chem.,* 264:12419–12425.

Huber (1986) "Use of baculoviruses in pest management programs," in *The Biology of Baculoviruses,* vol. II Granados and Federici, Eds., CRC Press, Boca Raton, Fl. pp. 181–202.

Huybrechts et al., (1992) "Nucleotide sequence of a trans-activating *Bombyx mori* nuclear polyhedrosis virus immediate early gene" *Biochim. Bioph. Acta* 1129:328–330.

Iatrou et al. (1985) "Polyhedrin gene of *Bombyx mori* nuclear polyhedrosis virus," *Journal of Virology,* 54:436–445.

Iatrou et al. (1988) "Towards the development of a vector for transducing homologous and foreign genes into silkmoth tissue culture cells and animals," in *Endoctrinological Frontiers in Physiological Insect Ecology,* Eds. Sehnal et al., Wroclaw Technical University Press, Wroclaw, pp. 1055–1073.

Iatrou et al. (1989) "Recombinant baculoviruses as vectors for identifying proteins encoded by intron–containing members of complex multigene families," *Proc. Natl. Acad. Sci. USA,* 86:9129–9133.

Iatrou and Meidinger (1989) "*Bombyx mori* nuclear polyhedrosis virus–based vectors for expressing passenger genes in silkmoth cells under viral or cellular promoter control," *Gene,* 75:59–71.

Iatrou and Meidinger (1990) "Tissue–specific expression of silkmoth chorion genes in vivo using *Bombyx mori* nuclear polyhedrosis virus as a transducing vector," *Proc. Natl. Acad. Sci. USA,* 87:3650–3654.

Iatrou et al. (1992) "Recombinant baculoviruses for lepidopteran insect pest control," *Sericologia 31,* Suppl. 78 [Abstract].

Johnson et al. (1992) "A Cellular Promoter–Based Expression Cassette for Generating Recombinant Baculoviruses Directing Rapid Expression of Passenger Genes in Infected Insects," *Virology,* 190:815–823.

Kamita et al., (1993) "Identification and characterization of the p35 gene of *Bombyx mori* nuclear polyhedrosis virus that prevents virus–induced apoptosis" *J. Virol.* 67:455–463.

Kang, C.Y. (1988) "Baculovirus vectors for expression of foreign genes," *Adv. Virus Res.* 35:177–192.

Kang, C.Y. "Improved Baculovirus Expression System Capable of Producing Foreign Gene Proteins at High Levels," University of Ottawa Fact Sheet.

Keddie et al. (1989) "The pathway of infection of *Augographa californica* nuclear polyhedrosis virus in an insect host." *Science* 243:1728–1730.

Kool et al., (1993) "Location of two putative origins of DNA replication of *Autographa californica* nuclear polyhedrosis virus" *Virology* 192:94–101.

Kovacs et al. (1991) Novel regulatory properties of IE1 and IE0 transactivators encoded by the baculovirus *Autographa californica* multicapsid nuclear polyhedrosis virus, *J. Virol.,* 65:5281–5288.

Kunkel (1985) "Rapid and efficient site–specific mutagenesis without phenotypic selection," *Proc. Natl. Acad. Sci. USA,* 82:488–492.

Maeda et al. (1991) "Insecticidal effects of an insect–specific neutrotoxin expressed by a recombinant baculovirus," *Virology,* 184:777–780.

Maeda (1989) "Expression of foreign genes in insects using baculovirus vectors," *Ann. Rev. Entomol.,* 34:351–372.

Maeda (1989) "Increased insecticidal effect by a recombinant baculovirus carrying a synthetic diuretic hormone gene," *Biochem. Biophys. Res. Commun.,* 165:1177–1183.

Maeda and Majima (1990) "Molecular cloning and physical mapping of the genome of *Bombyx mori* nuclear polyhedrosis virus" *J. Gen. Virol.* 71:1851–1855.

Majima et al. (1993) "Divergence and evolution of homologous regions of *Bombyx mori* nuclear polyhedrosis virus" *J. Virol.* 67:7513–7521.

Maxam and Gilbert (1977) " A new method for sequencing DNA," *Proc. Natl. Acad. Sci. USA,* 74:560–564.

McCutcheon et al. (1991) "Development of a recombinant baculovirus expressing an insect–selective neurotoxin: potential for pest control," *Bio/Technology,* 9:848–852.

Merryweather et al. (1990) "Construction of genetically engineered baculovirus insecticides containing the *Bacillus thuringiensis* subsp. *kurstaki* HD–73 delta endotoxin," *Journal of General Virology,* 71:1535–1544.

Miller (1988) "Baculoviruses as gene expression vectors," *Ann. Rev. Microbiol.,* 42:177–199.

Miller (1989) "Insect baculoviruses: Powerful gene expression vectors," *BioEssays,* 11:91–95.

Mitsialis et al. (1987) "A short 5'–flanking DNA region is sufficient for developmentally correct expression of moth chorion genes in Drosophila," *Proc. Natl. Acad. Sci. USA,* 84:7987–7991.

Mounier and Prudhomme (1986) "Isolation of actin genes in *Bombyx mori:* the coding sequence of cytoplasmic actin gene expressed in silk gland is interrupted by a single intron in an unusual position," *Biochimie,* 68:1053–1061.

Mounier and Prudhomme (1991) "Differential expression of muscle and cytoplasmic actin genes during development of *Bombyx mori,*" *Insect Biochem.,* 21:523–533.

Nissen and Friesen (1989) "Molecular analysis of the transcriptional regulatory region of an early baculovirus gene" *J. Virol.* 63:493–503.

Oliva and Dixon (1989) "Chicken protamine genes are intronless," *J. Biol. Chem.* 264:12472–12481.

Pearson et al., (1992) "The *Autographa californica* baculovirus genome: evidence for multiple replication origins" *Science* 257:1382–1384.

Pen et al. (1989) "An efficient procedure for the isolation of recombinant baculovirus," *Nucl. Acids Res.,* 17:451.

Possee and Howard (1987) "Analysis of the polyhedrin gene promoter of the *Autographa californica* nuclear polyhedrosis virus," *Nucl. Acids Res.,* 15:10233–10248.

Price et al. (1989) "Complementation of recombinant baculoviruses by coinfection with wild–type virus facilitates production in insect larvae of antigenic proteins of hepatitis B virus and influenza virus," *Proc. Nat'l. Acad. Sci. USA*, 86:1453–1456.

Sambrook et al. (1989) "Molecular Cloning: A Laboratory Manual," Cold Spring Harbor Laboratory Press. pp. xi–xxxviii.

Schneider and Taghert (1990) "Organization and Expression of the Drosophila Phe–Met–Arg–Phe–$NH_2$ neuropeptide gene," *J. Biol. Chem.*, 265:6890–6895.

Sivasubramanian and Hice "Development of novel genetically engineered antisense insect viruses as improved viral insecticides", [Abstract only].

Skinner et al. (1991) "Isolation and identification of paralytic peptides from hemolymph of the Lepidopteran insects *Manduca sexta, Spodoptera exigua,* and *Heliothis virescens,*" *Journal of Biological Chemistry*, 266:12873–12877.

Smith et al. (1983) "Production of human beta interferon in insect cells infected with a baculovirus expression vector," *Mol. Cell, Biol.*, 3:2156–2165.

Starrat and Brown (1975) "Structure of the pentapeptide proctolin, a proposed neurotransmitter in insects," *Life Sciences*, 17:1253–1256.

Stavroulakis et al. (1991) "Kinetic data for the BM–5 insect cell line in repeated–batch suspension cultures," *Biotechnology and Bioengineering*, 38:116–126.

Stavroulakis et al. (1991) "Growth characteristics of a *Bombyx mori* insect cell line in stationary and suspension cultures," *The Canadian Journal of Chemical Engineering*, 69:457–464.

Stewart et al., (1991) "Construction of an improved baculovirus insecticide containing an insect–specific toxin gene," *Nature*, 352:85–88.

Summers (1991) "Baculovirus–directed foreign gene expression," in Insect Neuropeptides, Eds. Menn et al., *American Chemical Society Symposium Series*, No. 453, pp. 237–251.

"Method to produce highly toxic and virulent viral insecticides," (Apr. 1991) *Technology Access Report University of California* [Abstract only].

Tomalski and Miller (1991) "Insect paralysis by baculovirus–mediated expression of a mite neurotxin gene," *Nature,* 352:82–85.

Wang et al. (1991) "Baculovirus vectors for multiple gene expression and for occluded virus production," *Gene,* 100:131–137.

Wood and Granados (1991) "Genetically engineered baculoviruses as agents for pest control," *Ann. Rev. Microbiol.,* 45:69–87.

Zilberberg et al. (1991) "The cDNA sequence of a depressant insect selective neurotoxin from the scropion *Buthotus judaicus," Toxicon,* 29:1155–1158.

Zuidema et al. (1990) "Expression of cauliflower mosaic virus gene I in insect cells using a novel polyhedrin–based baculovirus expression vector" *Journal of General Virology* 71:2201–2209.

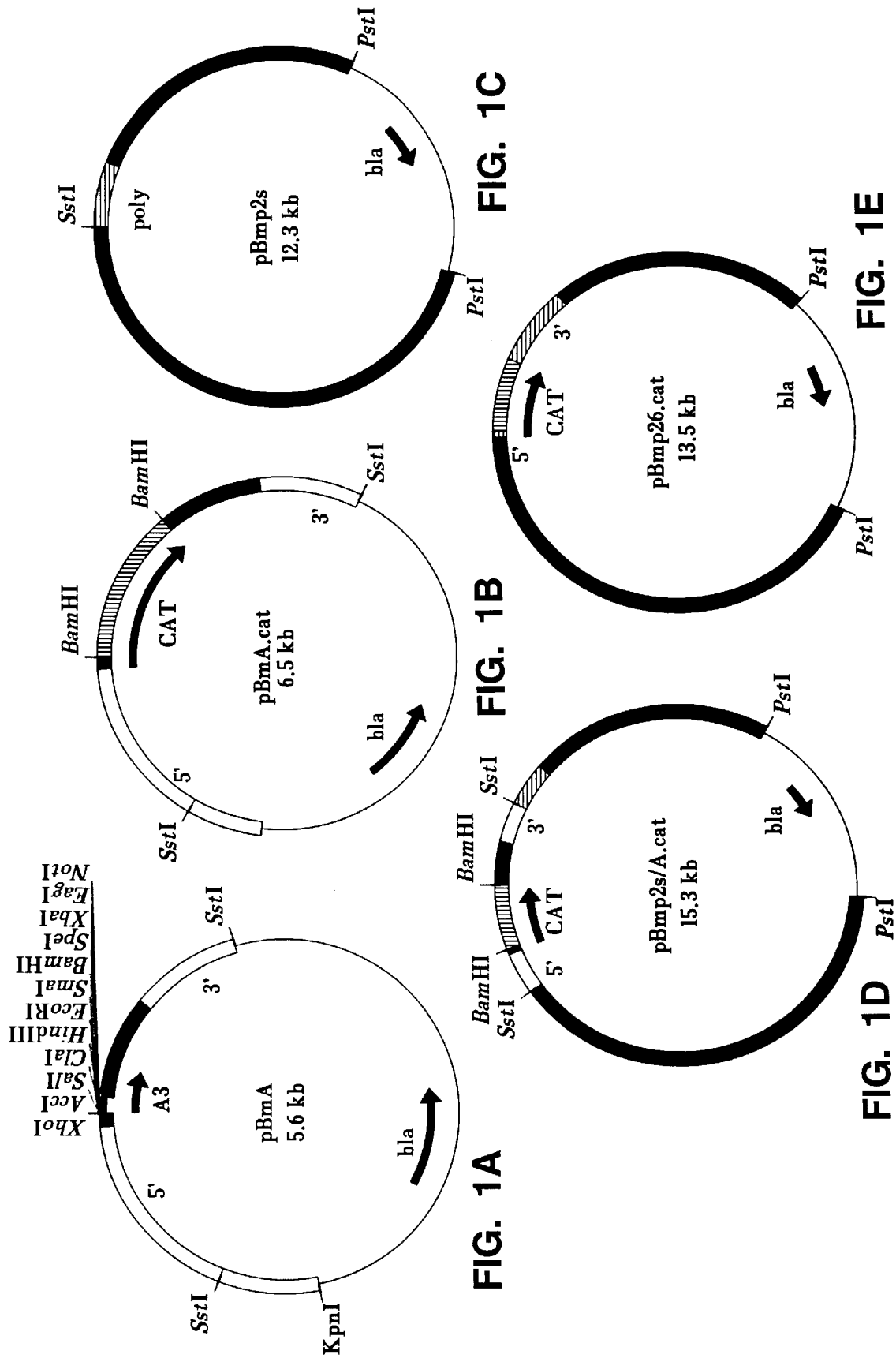

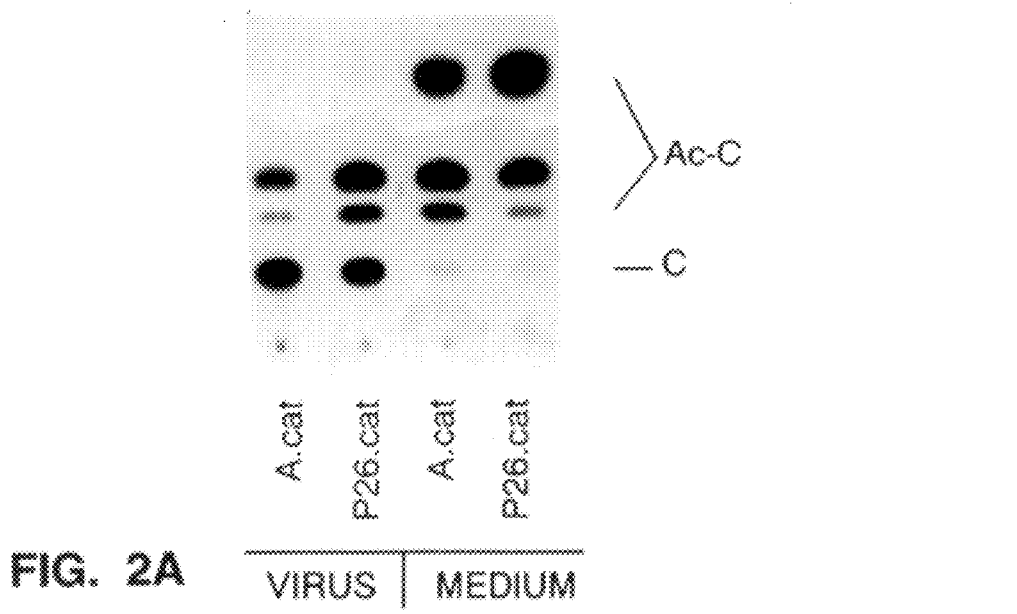
FIG. 2A
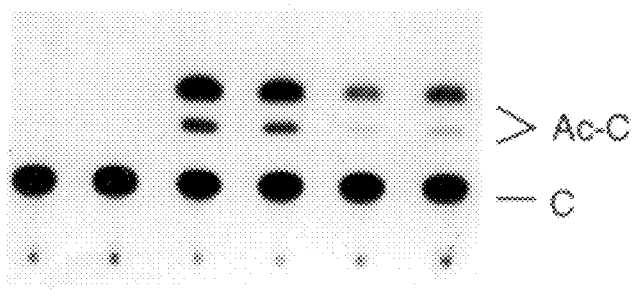
FIG. 2B
FIG. 2C

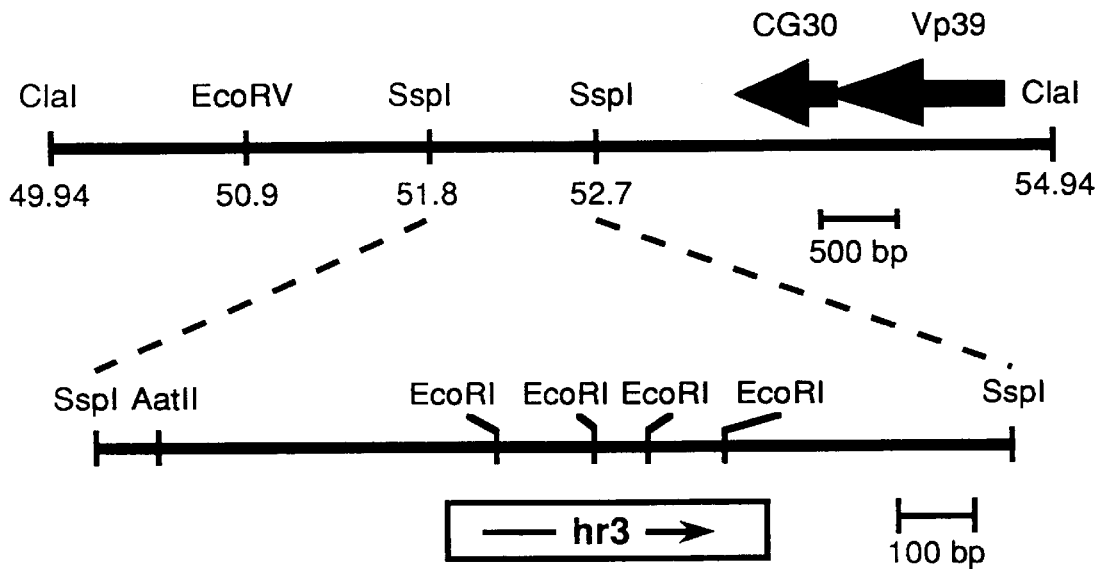

FIG. 9A

```
AATATTAGAC AACAAAGATT TATTTTATTC ATGCCACTAC TCGGTTCCGT TTTTCAAGCT
AACCAGTTGT CATGCGGAAA ATGACGTCAT TATTAATGCT TTAAACGAGT TACGCAACAA
CGTTAAAGTG GACGCTGATT GCGATTTTTT TCaaaGACCT ATCGCACGTT TaAAACGCGT
ACGCTTATGT GGGCAACGGG ATTGGTTGTA GATCCGCGTA CGACGAAGAT GCGATAGTGG
TAAAAAAAGA AGCCGTGCCC AGTCACGTGT ACGCCAACCT GAACACGCAA TCCAACGACG
GCGTCAAATA CAATCGTTGG TTGCACGTTA AAAACGGCCA ATACATGGCG TGTCCTGAAG
AATTGTACGA TAACAACGAA TTTAAATGTA ACGTAGAATC GGATAAATTA TATTATTTGG
ATAATTTACA AGAAGATTCC GTTGTATAAA CATTTTATGA CGAAAACAAA TGACATCATT
CCTGATTATA ATAATTTTAA TCGTGCGTTA CAAGTAGAAT TCTACTTGTA AAGCGAGTTT
AATTTGAAAA ACAAATTAGT CATTATTAAA CATGTTAACA ATCGTGTATA AAAATGACAT
CAGTTTAATG ATGACATCAT CTCTTGATTA TGTTTTACAC GTAGAATTCT ACTCGTAAAG
CCGGTTCAGT TTTGAAAAAC AAATGACATC ATCTCTTGAT TATGTTTTAC ACGTAGAATT
CTACTCGTAA AAGCGAGTTT AGTTTTAAAA AACAAATGAC ATCATTCAGT TTTGAAAAAC
AAATGACATC ATCTCTTGAT TGTGTTTTAC AAGTAGAATT CTACTCGTAA AGCGAGTTCA
GTTTTGAAAA ACAAATGACC CTCTCATACA ATCGTTGAAC AATTTTAATA AATAATCTTT
ACAAGATTCG TTTGAAGGCC TCATAAACAA TTTATATGAT TTAATATCAA TATACTTTTT
CAATCTAGCC TCGAATGGGC TGTTCACAAA TTACGCTTCT TCCACAATAA TTGCGTCGTA
GCAAATTGCC AAATACTTGA CGCAACTAAT AACGTCTGAA TGGGTTTCAT CTTGAGCGCA
CCTCCATCAT CAAAATCATA AAACGATCTA TTTGTGGGCC AAGCTGCTGT ACCGTATAAA
TCGTATAATA CGACGCGGAG AAATTAATTT CTGGCACGAA CGTAATATT
```

FIG. 9B

METHODS OF EXPRESSING PROTEINS IN INSECT CELLS AND METHODS OF KILLING INSECTS

This application is a divisional of application Ser. No. 08/608,617, filed Mar. 1, 1996 now U.S. Pat. No. 5,759,809, which is a continuation of application Ser. No. 08/172,653, filed on Dec. 23, 1993, now abandoned.

BACKGROUND OF THE INVENTION

1. Field of the Invention

The present invention relates to a method of expressing heterologous proteins in insect cells using genetic elements which potentiate activity of an insect cellular promoter functionally attached to a structural gene for a heterologous protein. The heterologous protein may include proteins toxic or harmful to an insect host or proteins whose unregulated expression will incapacitate the insect host. The invention is also directed to expression cassettes, recombinant expression cassettes containing heterologous genes, transplacement fragments containing expression cassettes, transplacement fragments containing recombinant expression cassettes, vectors containing transplacement fragments and recombinant baculoviruses derived therefrom.

2. State of the Art

Nuclear polyhedrosis viruses (NPVs) are a subgroup of the family Baculoviridae, whose virions are embedded into proteinaceous polyhedra in the nucleus of host cells. Baculoviruses provide alternatives to chemicals for controlling insect pests. Because most NPVs have a host range restricted to only a few closely related species, they can be used without disrupting the balance of other insect and non-insect species (e.g. important predators) in the agricultural ecosystem. No baculovirus has been demonstrated to infect mammals, reptiles, birds, invertebrates such as earthworms or plants. To date, however, baculoviruses have met with only limited commercial success as control agents, due to difficulties with virus stability and, most importantly, slower speed of action than that achieved with chemical insecticides.

Certain baculoviruses, specifically nuclear polyhedrosis viruses (NPVs), have a unique life cycle which involves the temporally regulated expression of two functionally and morphologically different viral forms, the budded form and the occluded form. Nuclear polyhedrosis viruses produce large polyhedral occlusion bodies, which contain enveloped virus particles, within the nucleus of infected cells. The occlusion body is composed of a matrix comprising a 29 kDa protein known as polyhedron. After the insect dies from infection, occlusion bodies containing virus are released from the dead larvae into the environment and spread the infection to other insects through contamination of the food supply. These occlusion bodies serve to protect the virus particles in the environment and also provide a means of delivering the virus particles to the primary site of infection in insects, the midgut epithelial cells. When the occlusion bodies are ingested by the larvae, the alkaline pH of the midgut lumen of phytophagous lepidopteran larvae dissolves the paracrystalline matrix in which the virus particles are embedded, promoting infection.

Secondary infection within the insect involves the budded form of the virus. Viral nucleocapsids are synthesized in the nucleus of the insect cell, move through the cytoplasm and bud from the plasma membrane of the cell resulting in the release of budded virus particles into the insect hemolymph. The open circulatory system of the insect provides the virus with access to other tissues of the insect. Virtually all tissues within the host larvae are susceptible to infection by the budded virus. Replication of the virus in other organs creates extensive tissue damage and eventually death. Generally, the complete process can take 4–5 days in the laboratory, but may take more than a week in the field.

The synthesis of the budded and occluded forms of the virus is temporally regulated. During a typical infection of host tissue culture cells, progeny budded viruses are released into the culture media beginning approximately 12 hour post infection (p.i.) and the release continues logarithmically through 22 hours p.i. Occluded virus forms approximately at 20 hours p.i. and continues through 70 hours p.i. by which time approximately 70–100 polyhedral occlusions have formed in the nucleus. This temporal regulation of viral development is reflected in the controlled transcription of specific viral genes.

Nuclear polyhedrosis virus genes are transcribed in a regulated cascade involving at least three phases of transcription: an early phase (0–6 hours p.i.) prior to viral DNA replication, a late phase (6–18 hours p.i.) involving DNA replication and budded virus formation and the very late occlusion phase (18 through 70 hours p.i.).

In contrast to chemical pesticides which usually act upon the target insect immediately upon application, baculovirus infection-mediated reduction of the population of insects occurs in the field only one to two weeks after application of wild-type baculovirus. In order to increase the speed of insect inactivation by baculoviruses, recombinant viruses have been generated which express non-viral proteins whose products are toxic to the infected insect, under the control of viral or synthetic promoters. The underlying premise for the creation of such recombinant viruses has been that the expression of the foreign protein in the larvae should inactivate or kill the larvae before they would normally succumb to viral infection. Some recombinant viruses have been developed which employ the viral polyhedron promoter (Merryweather et al., 1990; Tomalski and Miller, 1991; Maeda et al., 1991), the viral p10 promoter (Stewart et al., 1991; McCutchen et al., 1991), or a synthetic promoter based on the previous two (Wang et al., 1991) to express the desired foreign protein. While these viral promoters can direct the expression of high levels of protein, they are not expressed until the very late occlusion stage of infection.

One of the key aspects of the development of recombinant baculoviruses as effective insecticides is the timing and site of expression of heterologous proteins following initial infection of the target insect. When larvae are infected orally with relatively low doses of polyhedra, as would normally occur under field conditions, the first cells to be infected are the columnar and regenerative cells of the midgut epithelium. The generalized spread of the virus to other tissues of an infected larva through circulation does not occur until 36 hours after the virus is first observed in the gut epithelium. Expression of heterologous genes under the control of the polyhedron or p10 promoters in vivo may not occur until an even later time as there is some doubt as to the level of expression of genes under the control of the viral polyhedron or p10 promoters in the epithelial cells of the midgut, the primary site of infection, as normal production of polyhedra is not observed in these cells (Granados and Lawler, 1981). Thus, placing an insect incapacitating or toxic gene under the control of the polyhedron or p10 promoter may offer modest advantages in the order of only 1 or 2 days in terms of accelerating insect death relative to an infection with a wild type baculovirus.

Because early viral promoters are usually essential and cannot be deleted, their utilization as the promoter for the toxin gene would require the presence of a duplication of the promoter sequence in the viral genome. Recombinant viruses containing such duplications of early viral promoters may prove unstable over the many large-scale passages necessary for commercial production.

A recombinant virus has also been developed which contains silkmoth chorion chromosomal genes under the control of their own promoter (Iatrou and Meidinger, 1990). The transcripts from this recombinant virus are expressed correctly only in the tissue in which this promoter is normally active, ovarian follicular cells of the insect, but not in any other tissues, for example fat body, other tissues of the abdomen such as muscles or ganglia or in non-expressing tissue culture cells such as Bm5 cells. Further, because of the presence of a thick basement membrane that completely surrounds each follicle, the later recombinant virus infects the follicle cells only in a limited fashion and only after a considerable time lag (e.g., 36–48 hours) after in vitro inoculation (injection) of the insect with the virus.

Advances in the genetics of invertebrate viruses and cells have allowed the development of viral-cellular systems which give both a high level of synthesis and complex processing of recombinant products. In particular baculoviruses such a *Autographica californica* nucleopolyhedrosis virus (AcNPV) and *Bombyx mori* (BmNPV) nucleopolyhedrosis virus are extremely useful helper-independent eukaryotic vectors. Both of these systems are based on the utilization of the strong promoter of the gene encoding polyhedron. The techniques conventionally employed in these systems are described in U.S. Pat. No. 4,745,051 and U.S. Pat. No. 5,194,376 both of which are incorporated by reference in their entirety herein. This system has been used for the successful production of large quantities of many different gene products. One difficulty with this system is the cells eventually die because they are infected with a virus.

The hr's are repeated sequences present in several baculoviruses, including Autographica californica nuclear polyhedrosis virus (AcNPV) (Cochran and Faulkner, 1983; Guarino and Summers, 1986; Guarino et al., 1986) and BmNPV (Maeda and Majima, 1990; Kamita et al., 1993). The hr elements have been shown to serve as origins of replication in AcNPV and can, under some conditions, allow plasmids containing these sequences to replicate in AcNPV-infected cells (Pearson et al., 1992; Kool et al., 1993). The hr's of AcNPV (designated hr1 through hr5) have been previously shown to serve as strong enhancers for early viral genes such as the 39K gene (Guarino and Summers, 1986; Guarino et al, 1986), the 35K gene (Guarino and Summers, 1987; Nissen and Friesen, 1989), and the IE-N gene (Carson et al., 1991). Expression of other baculovirus genes, however, such as the IE-1 gene (Guarino and Summers, 1986) and the polyhedron gene, is not stimulated by the hr elements. The AcNPV hr5 has also been demonstrated to enhance a promoter of non-baculovirus origin, the Rous Sarcoma Virus long terminal repeat (RSV LTR) promoter (Guarino and Summers, 1986). In the case of the RSV LTR promoter, the 35 promoter, (Nissen and Friesen, 1989), and the IE-N promoter, hr enhancers were able to stimulate transcription in the absence of the IE-1 gene product. The hr enhancers were only able to stimulate transcription from the 39K promoter, however, in the presence of the IE-1 protein. An hr enhancer-binding protein was detected in insect cells after transfection with the AcNPV IE-1 gene, but no binding activity could be detected in normal cells (Guarino and Dong, 1991).

The IE-1 gene product is a gene product which is expressed by the baculovirus genome at the early stages of infection under the control of the transcriptional machinery of the insect cell. Upon expression the gene product stimulates the expression of the p39 and IE-N genes of the baculovirus genome (Carson et al., 1988).

SUMMARY OF THE INVENTION

In one of its method aspects the invention is directed to a method of incapacitating insects comprising infecting an insect with an active recombinant baculovirus, such baculovirus comprising a structural gene encoding an incompatible protein functionally linked to an insect cellular promoter and an enhancer under conditions where the incompatible protein is expressed in the insect having the recombinant baculovirus present therein.

In the second of its method aspects the invention is directed to a method of producing heterologous protein in insect cells comprising expressing the heterologous protein from a enhanced recombinant expression cassette such cassette comprising a structural gene encoding the heterologous protein functionally linked to an insect cellular promoter and an enhancer.

In a third method aspect, the invention is directed to a method of producing heterologous protein in insect cells wherein the insect cells comprise an IE-1 gene under conditions wherein the IE-1 product is produced, such method comprising expressing the heterologous protein from a recombinant expression cassette, such cassette comprising a structural gene encoding a protein functionally linked to an insect cellular promoter.

In one of its product aspects the invention is directed to an expression cassette comprising an insect cellular promoter and an enhancer wherein the insect cellular promoter is capable of expressing a heterologous gene functionally linked to the promoter. The invention is also directed to recombinant expression cassettes, transplacement fragments and transplacement vectors having the enhanced expression cassette.

In another of its product aspects, the invention is directed to an insect cell comprising the IE-1 gene in the absence of added baculovirus.

BRIEF DESCRIPTION OF THE DRAWINGS

FIG. 1—Plasmid Vectors Used in the Generation of Recombinant Viruses

A. This is a schematic representation of the vector pBmA. The 5' and 3' flanking sequences of the cytoplasmic actin gene are represented by the unfilled regions and the transcribed sequences are indicated by the shaded region. The line represents sequences from pBS/SK+ containing the beta-lactamase (bla) gene which confers ampicillin resistance. All of the restriction enzyme sites shown in the multiple cloning site are unique in this plasmid.

B. This is a schematic representation of the vector pBmA.cat. The region containing vertical lines represents the cat gene open-reading frame. All other designations are as in A.

C. This is a schematic representation of the vector pBmp2s. The region containing horizontal lines represents the deleted polyhedron gene containing no promoter sequences. Black regions represent sequences flanking the polyhedron gene in the BmNPV genome. The line represents pUC9 DNA.

D. This is a schematic representation of the vector pBmp2s/A.cat. The line represents DNA from pBS/SK+. All other designations are as described in A and C.

E. This is a schematic representation of pBmp26.cat. The region containing horizontal lines represents the polyhedron gene including all sequences necessary for strong promoter activity. All other designations are as described in C.

FIG. 2—Analysis of CAT Activity in Non-Occluded Virus

A. Non-occluded virus from cells transfected with pBmNPV/A.cat or pBmNPV/P26.cat was separated from the medium as described in Example 2 and the level of CAT determined. The upper spots (Ac-C) represent acetyl chloramphenicol, the products of the CAT reaction, while the lower spot in each assay (C) represents the substrate, chloramphenicol.

B. Bm5 cells were assayed for CAT activity at the indicated times after addition of BmNPV/A.cat or BmNPV/P26.cat inoculum. Assays were performed using the amount of cell protein and length of incubation indicated and as described in Example 5.

C. Bm5 cells were infected with the standard inoculum containing medium and virus (M+V), with non-occluded virus isolated from the inoculum (V), or mock infected (----). The cells were collected 1 hour after infection and were washed once (1×) or five times (5×) with 1 ml PBS.

Figure 3A:
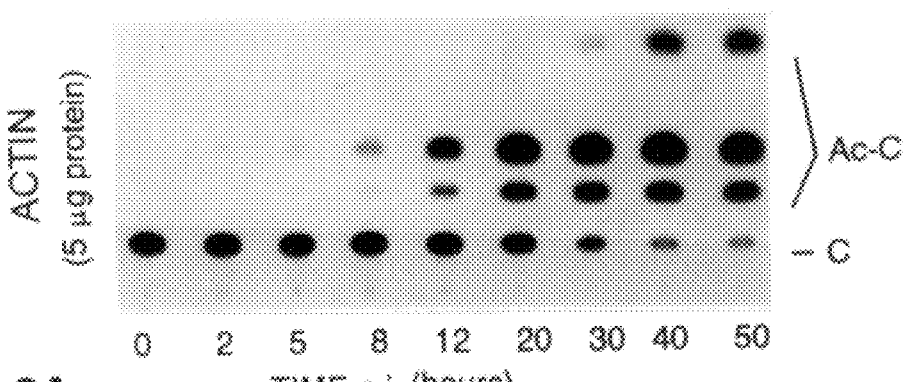

FIG. 3—Time Course of CAT Activity in Infected Bm5 Cells

Cells were infected and assayed as described in Example 6.

A. Cells were infected with BmNPV/A.cat inoculum and CAT assays were performed at the indicated time post infection using 5 μg cell protein incubated for 1 hour.

B. Cells were infected with BmNPV/P26.cat inoculum and assayed using 1 μg cell protein incubated for 1 hour at the indicated times post infection.

C. Appropriate amounts of cell extract from cells infected with BmNPV/A.cat (actin) or BmNPV/P26.cat (polyhedron) were assayed to quantitate CAT assays at each time point. The background CAT activity observed at 1–2 hours p.i. was subtracted from each point. The values were plotted on a logarithmic scale.

Figure 4:
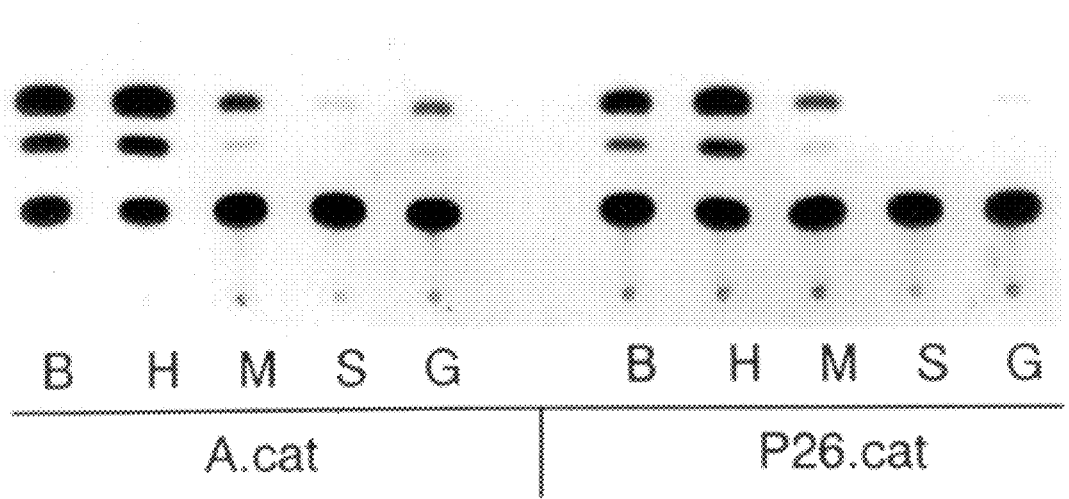

FIG. 4—Analysis of CAT Activity in Infected Larvae

Fifth instar larvae were injected with either BmNPV/A.cat or BmNPV/P26.cat inoculum and after 2 days were assayed for CAT activity in body wall (B), head (H), midgut (M), silk gland (S), and gonad (G) as described in Example 7. Tissues from three larvae were pooled for each assay.

FIG. 5—Time Course of CAT Activity in Infected Larvae

Early fifth larvae were injected with either BmNPV/A.cat or BmNPV/P26.cat inoculum and were assayed for CAT activity in body wall tissues as described in Example 7 at various times p.i. Each point represents the average of two larvae. (Ac-C represents acetyl chloramphenicol; C is the substrate chloramphenicol.)

A. CAT assays of body wall tissues from larvae injected with BmNPV/A.cat.

B. CAT assays of body wall tissues from larvae injected with BmNPV/P26.cat.

C. Appropriate amounts of body wall tissue from larvae injected with BmNPV/A.cat (solid circles) or BmNPV/P.26cat (open circles) were assayed for CAT activity, the background level of CAT activity observed at 2–4 hr p.i. was subtracted and the values plotted on logarithmic scale.

FIG. 6—Transfection of Cells with pBmA.cat

Tissue culture cells (Bm5 or Sf21) were transfected as described in Example 8. (Ac-C represents acetyl chloramphenicol; C represents the substrate chloramphenicol).

A. CAT assays performed on the indicated amount of culture cells 2 days after cells were transfected with pBmA.cat.

B. The amount of plasmid DNA present in the transfected cells was measured by dot-blot hybridization of the indicated amount of cell suspensions, using as a probe radioactively labelled pBS/SK+ DNA, as described in Example 8.

Figure 7:

FIG. 7—Southern Blot Analysis of the Contents of Polyhedra from Mixed Infections This is an autoradiogram of DNA from Bm5 cells infected with virus released from occlusion bodies from cells infected with mixtures of pure wild type BmNPV ("WT") and BmNPV/A.cat ("A.cat") or pure wild type BmNPV ("WT")BmNPV/P26.cat ("P26.cat"). The lines designated A.cat and P26.cat alone are controls.

Figure 8A:
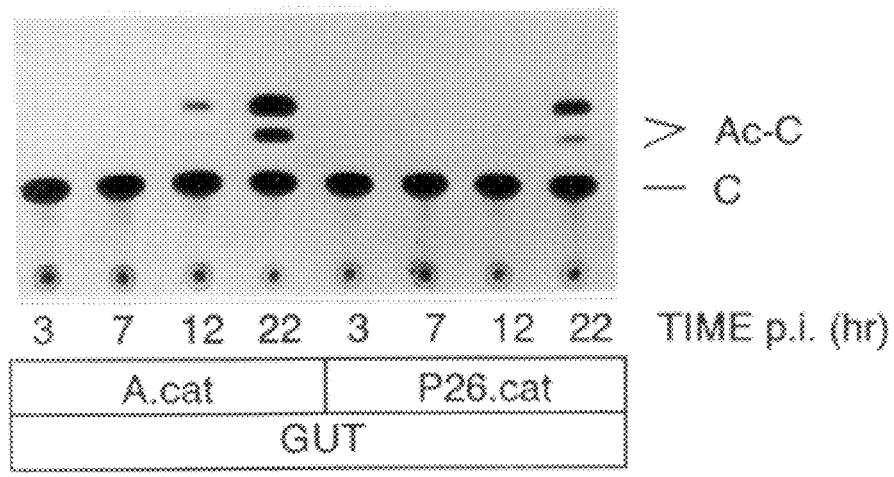
Figure 8B:
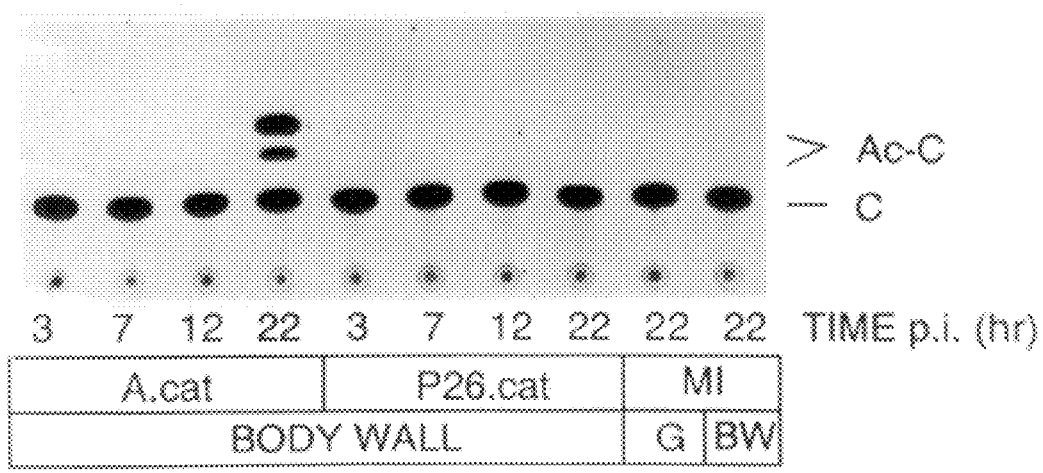

FIG. 8—Time Course of CAT activity in orally infected larvae

A. Gut ("G") from larvae infected with BmNPV/A.cat ("A.cat") or BmNPV/P26.cat ("P26.cat") were analysed at the indicated times for CAT activity. (Ac-C represents acetyl chloramphenicol; C represents the substrate chloramphenicol)

B. Mock infected ("MI") and body wall tissues ("BW") from larvae infected with BmNPV/A.cat ("A.cat") or BmNPV/P26.cat ("P26.cat") were analysed at the indicated times for CAT activity. (Ac-C represents acetyl chloramphenicol; C represents the substrate chloramphenicol).

FIG. 9—Location of hr3 in the BmNPV genome and its nucleotide sequence.

A. Physical map of part of the BmNPV genome showing restriction sites. Arrows indicate gene products GC30 and Vp39 from baculovirus genome.

B. The nucleotide sequence of the 1.2 kb Sspl fragment containing the hr3 sequence (SEQ ID NO:1). Box indicates region with homology to hr sequences. DNA sequence for EcoRI sites are italicized.

Figure 10A:
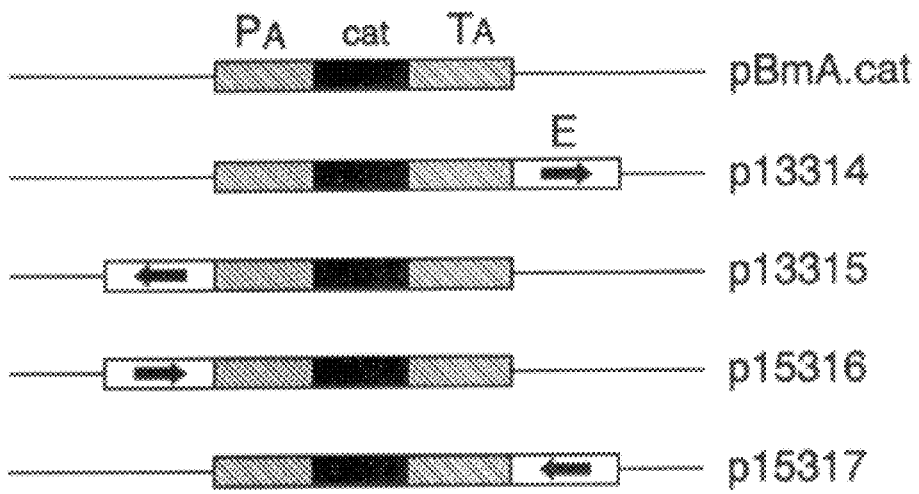
Figure 10B:
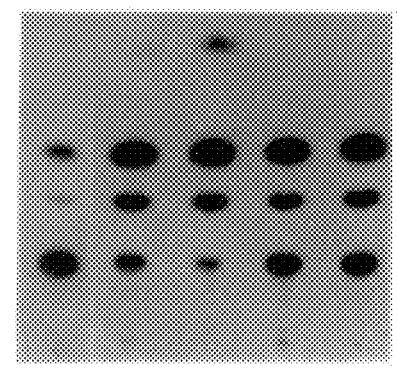
Figure 10C:
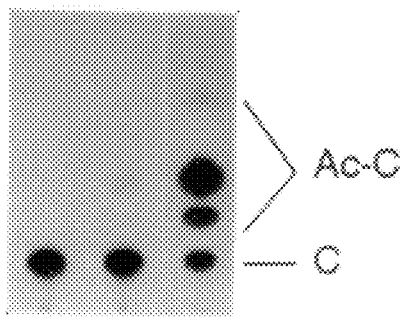

FIG. 10—Enhancement of the actin promoter in transfected cells.

A. Plasmids used for transfection containing the actin promoter ($P_A$), the chloramphenicol acetyl transferase coding region (cat), the actin terminator ($T_A$), and the 1.2 kb enhancer containing sequence (E). The arrow indicates the orientation of the enhancer sequence, as indicated in FIG. 9A.

B. CAT activity in Bm5 cells transfected with the plasmids in FIG. 10A and pBmA.cat. (Ac-C represents acetyl chloramphenicol; C represents the substrate chloramphenicol)

C. CAT activity in Sf21 cells transfected with the plasmids pBmA.cat and p13315. (Ac-C represents acetyl chloramphenicol; C represents the substrate chloramphenicol)

Figure 11A:
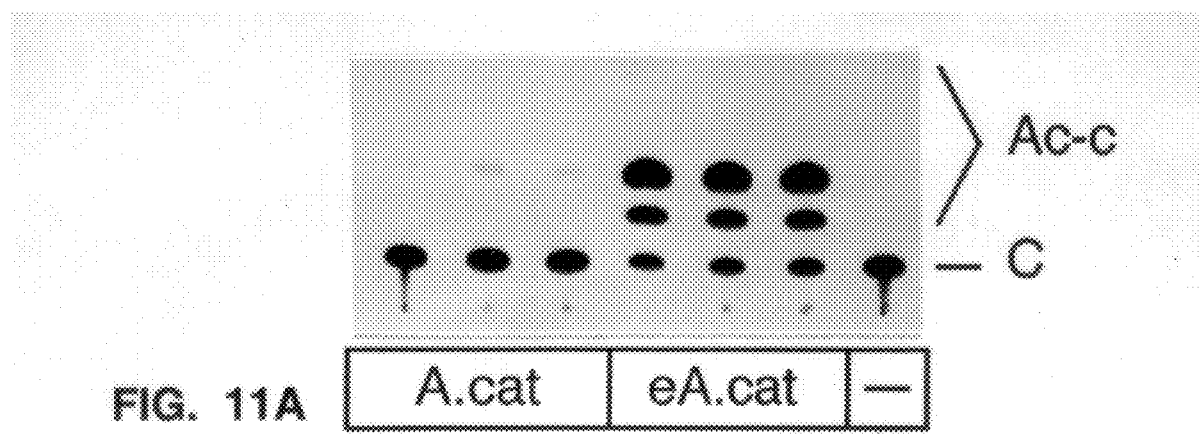
Figure 11B:
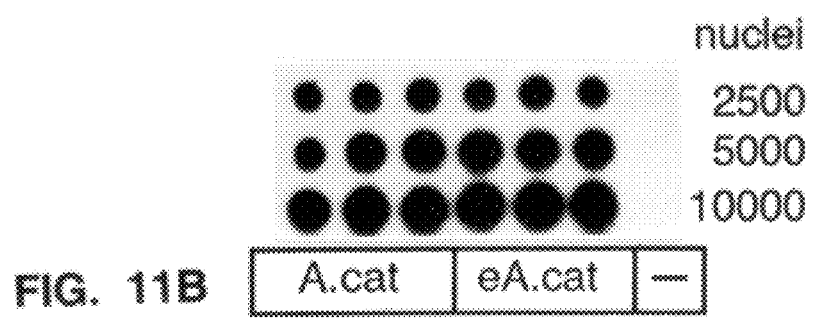

FIG. 11—Enhancement of the actin promoter in infected cells.

A. CAT activity of cells infected with BmNPV and transfected with pBmA.cat ("A.cat") or p13315 ("eA.cat"). (Ac-C represents acetyl chloramphenicol; C represents the substrate chloramphenicol)

B. Autoradiogram of DNA from nuclei of insect cells infected with BmNPV and transfected with pBmA.cat ("A.cat") or p13315 ("eA.cat"). Numbers indicate the number of nuclei dot blotted onto the membrane.

FIG. 12—Plasmids used in the generation of recombinant virus.

A. This is map of the plasmid pBMA. Vertical lines indicate the coding region of the B. mori cytoplasmic actin gene (A3) and the arrow indicates the direction of transcription. The single line indicates pBS/SK+sequences including the β-lactamase (bla) gene.

B. This is a map of the plasmid pBmeA. The 1.2 kb enhancer fragment is labelled "E" (shaded region). The other labels are as indicated in FIG. 12A.

FIG. 13—CAT assays of insect cells transfected with A.cat and either AcIE-1 or BmIE-1

A. CAT analysis of Bm5 cells transfected with pBmpA.cat alone, pBmpA.cat and pBmIE-1 or pBmpA.cat and pAcIE-1. (Ac-C represents acetyl chloramphenicol; C represents the substrate chloramphenicol)

B. CAT analysis of Sf21 cells transfected with pBmpA.cat alone, pBmpA.cat and pBmIE-1 or pBmpA.cat and pAcIE-1. (Ac-C represents acetyl chloramphenicol; C represents the substrate chloramphenicol)

Figure 14:
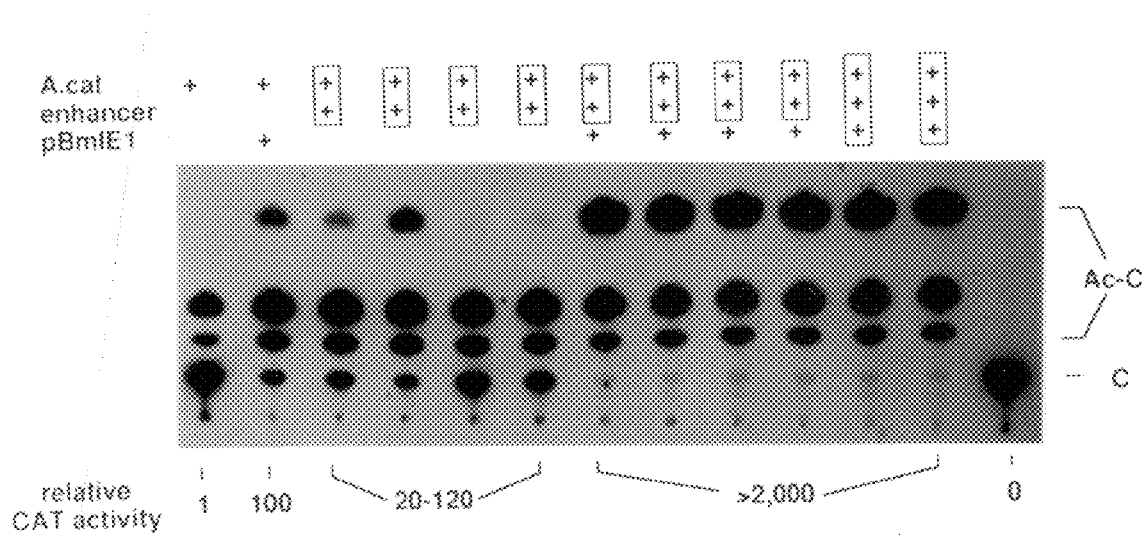

FIG. 14—CAT assays of insect cells transfected with different plasmids

"A.CAT" indicates the presence of the actin promoter, "pBmIE1" indicates the presence of the IE-1 structural gene and "enhancer" indicates the presence of the 1.2 kb enhancer element in the cells. The boxes indicate whether the elements are present on the same plasmid (inside the same box) or on different plasmids (i.e. different boxes). (Ac-C represents acetyl chloramphenicol; C represents the substrate chloramphenicol)

DETAILED DESCRIPTION OF THE INVENTION

As noted above, the present invention generally relates to a method of expressing heterologous proteins in insect cells using genetic elements which potentiate activity of an insect cellular promoter based expression cassette functionally attached to a structural gene for a heterologous protein. The heterologous protein may be a heterologous protein which is toxic to the insect or any other heterologous protein whose unregulated expression could incapacitate the insect host through unbalancing of an important physiological process. This invention is also related to expression cassettes containing insect cellular promoters and enhancers, recombinant expression cassettes containing heterologous genes functionally attached to insect cellular promoters, transplacement fragments containing recombinant expression cassettes, vectors having transplacement fragments, recombinant baculoviruses and insect cells derived therefrom.

The first genetic element is an enhancer which can stimulate the cellular promoter upon covalent linkage to the promoter. It has been found that depending on the specific promoter-enhancer linkage configuration the level of promoter activity potentiation relative to the activity of a recombinant expression cassette that lacks the enhancer is from about 40 fold to 100 fold. Further it has been found that transcriptional potentiation in insect cells is independent of viral infection. Rather the enhancers effect is mediated by cellular rather than viral factors. Further, the enhancer is equally active in cell lines derived from different lepidopteran insect species.

The second genetic element is a structural gene, IE-1, of the baculovirus genome which is expressed at the early stages of infection under the control of the transcriptional machinery of the cell. It has been found that this gene encodes a protein which acts as a transcriptional regulator. Upon expression, this protein stimulates the level of expression of heterologous gene products directed by the cellular promoter based expression cassette. This stimulation occurs in trans. i.e. the enhancing effect is the same irrespective of whether the gene encoding IE-1 is physically linked to the cellular promoter of the expression cassette in a vector or not. The enhancing effect of the IE-1 product on the cellular promoter in non-infected insect cells is approximately 100 fold. It has further been found that this effect is independent of the presence of the enhancer. Furthermore, the IE-1 gene is equally active in cell lines derived from a number of lepidopteran insects, for example Bombyx mori and Autographica californica. Also the IE-1 gene of AcNPV can substitute for that of BmNPV.

Addition of both genetic elements to the cellular promoter based expression cassette (the enhancer linked to the expression cassette and the IE-1 gene linked to the expression cassette or supplied separately to the cells in the form of a second plasmid) results in an increase in the expression of the heterologous proteins encoded by genes functionally linked to the cellular promoter.

This discovery has dual applications. The first utility is in the area of continuous high level expression of foreign genes in insect lines transformed with enhanced recombinant expression cassettes employing cellular promoters functionally linked to the foreign gene. To achieve continuous high level of expression of foreign genes, normal insect tissue culture cells can be transformed with a plasmid containing an enhanced expression cassette comprising a cellular promoter and the enhancer functionally linked to a foreign gene and an extra gene expressing a selective marker (e.g. antibiotic resistance gene under the control of a promoter that functions constitutively in insect cells, for example, the promoter of the IE-1 gene). Application of a relevant selection should lead to integration of one or more multiple copies of the plasmid into the chromosomes of the cells, thus generating an insect cell line capable of continuous high level expression of the foreign gene present in the recombinant expression cassette.

Alternatively, the insect cells can be transformed with a plasmid containing the IE-1 gene and a suitable resistance gene, thus generating a cell line expressing continuously the IE-1 gene product. Such a cell line can be subsequently transformed with additional plasmids containing the either the basic recombinant expression cassette or the enhanced recombinant expression cassettes and an additional gene conferring resistance to a second selection agent. In both cases, synthesis of the foreign protein will be continuous, because integrated expression cassettes cannot be lost through replication and the insect cells never die because they are not infected by any viruses. Expression will also occur at a high level.

The second application of this invention is in the development of recombinant baculoviruses for use as insect pest control agents. The discovery and utilization of the enhancer represents a significant improvement on the use of recombinant baculoviruses containing cellular promoter based expression cassettes. The use of the enhancer allows for enhanced, immediate and ubiquitous expression of foreign products from genes cloned into enhanced expression cassettes in insect infected with the corresponding enhanced recombinant baculoviruses. Only linkage of the enhancer to the cellular promoter is required in the case of recombinant baculoviruses since the IE-1 gene is produced in the infected cells by the baculovirus' genome immediately upon infection.

However, prior to discussing this invention in detail, the following terms will first be defined.

Definitions

The term "baculovirus" is used herein as an alternative to the term "nuclear polyhedrosis virus" or "NPV". It encompasses viruses classified under subgroup A of the family of Baculoviridae. Preferably it includes the viruses specific for the following insects: Bombyx sp. Autographica sp. and Spodoptera sp.

The term "expression cassette" means a fragment of nucleic acid comprising an insect cellular promoter sequence, with or without a sequence containing mRNA polyadenylation signals, and one or more restriction enzyme sites located downstream from the promoter allowing insertion of heterologous gene sequences. The expression cassette is capable of directing the expression of a heterologous protein when the structural gene encoding the heterologous protein is functionally attached to the insect cellular promoter by insertion into one of the restriction sites. The recombinant expression cassette allows expression of the heterologous protein in an insect when the expression cassette containing the heterologous protein is introduced into the tissues of the insect. Preferably the recombinant expression cassette allows expression at an early stage of infection and/or it allows expression in substantially all tissues of an insect. In one embodiment the expression cassette is that present in the plasmid pBmA.

The term "enhanced expression cassette" means a fragment of nucleic acid comprising an insect cellular promoter sequence and an enhancer, with or without a sequence containing mRNA polyadenylation signals, and one or more restriction enzyme sites located downstream from the promoter allowing insertion of heterologous gene sequences. The enhanced expression cassette is capable of directing the expression of a heterologous protein when the structural gene encoding the heterologous protein is functionally attached to the insect cellular promoter and the enhancer by insertion into one of the restriction sites. Preferably, the enhanced expression cassette is that DNA fragment present on plasmid pBmeA.

The term "recombinant expression cassette" means an expression cassette further comprising a structural gene sequence encoding a heterologous protein inserted into a restriction enzyme site such that the structural gene sequence is functionally linked to the insect cellular promoter. When the recombinant expression cassette is inserted into insect cells, the heterologous protein is expressed under the control of the insect cellular promoter. Preferably the recombinant expression cassette allows expression at an early stage of infection and/or it allows expression in substantially all tissues of an insect.

The term "recombinant enhanced expression cassette" means an enhanced expression cassette further comprising a structural gene sequence encoding a heterologous protein inserted into a restriction enzyme site such that the structural gene sequence is functionally linked to the insect cellular promoter and the enhancer. When the recombinant expression cassette is inserted into insect cells, the heterologous protein is expressed under the control of the insect cellular promoter and the enhancer.

The term "transplacement fragment" means a DNA fragment which comprises: (1) an expression cassette sequence or a recombinant expression cassette sequence, and (2) a portion of a baculovirus genome that can sustain insertions of non-viral DNA fragments. The term "enhanced transplacement fragment" means a DNA fragment which comprises: (1) an enhanced expression cassette sequence or a recombinant enhanced expression cassette sequence, and (2) a portion of a baculovirus genome that can sustain insertions of non-viral DNA fragments. The term "a portion of a baculovirus genome that can sustain insertions of non-viral DNA fragments" means a portion of the genome into which non-viral DNA fragments can be inserted or which can be replaced with the non-viral DNA fragments without affecting viral infectivity, replication or assembly. This portion of the genome should be of sufficient size to allow recombination events to occur between the transplacement vector or enhanced transplacement vector and a wild type baculovirus genome such that the expression cassette or enhanced expression cassette is inserted into the genome. One skilled in the art would know the size of the baculovirus flanking sequences necessary to allow recombination events. Preferably, the size of the baculovirus flanking sequences are at least about 500 bp on each side of the expression cassette, more preferably, the size of the flanking sequences is at least about 5,000 bp on each side.

In one embodiment, the sequence from the baculovirus genome comprises the 5' and 3' sequences of the polyhedron gene of the *B. mori* baculovirus. In another embodiment, the portion of the baculovirus genome contains the polyhedron gene and flanking sequences of the baculovirus AcNPV.

The term "transplacement vector" means nucleic acid which comprises: (1) a transplacement fragment, and (2) DNA sequences allowing replication and selection in bacteria, for example *E. coli*. An "enhanced transplacement vector" comprises an enhanced transplacement fragment and the bacterial DNA sequences. The vector may be a plasmid, another virus or simply a linear DNA fragment. A transplacement fragment or vector is used to produce recombinant baculoviruses through double recombination/cross-over events. When insect cells are transfected with the transplacement vector and DNA from wild-type baculovirus, a double cross-over event between the homologous portions of the baculovirus genome and the transplacement fragment will result in the replacement of a portion of the wild-type baculovirus sequence with the part of the transplacement fragment which contains the recombinant expression cassette.

The term "recombinant baculovirus" refers to a baculovirus whose genome comprises a recombinant expression cassette of the invention. An "enhanced recombinant baculovirus" means a baculovirus comprising a recombinant enhanced expression cassette. In one embodiment, the recombinant baculovirus comprises *B. mori* nuclear polyhedrosis virus in which a section of the DNA sequence encoding the polyhedron gene is replaced with a transplacement fragment comprising a heterologous structural gene functionally linked to an insect cellular promoter, preferably the promoter for the cytoplasmic actin gene of *B. mori*. In another embodiment, the recombinant baculovirus comprises *A. californica* nuclear polyhedrosis virus in which a transplacement fragment is inserted into a position on the genome 40 bp upstream of the polyhedron gene.

The term "promoter" means a DNA sequence which initiates and directs the transcription of a heterologous gene into an RNA transcript in cells.

An "insect cellular promoter" is a promoter which will direct the expression of a heterologous structural gene when the gene is functionally linked to the insect cellular promoter in a recombinant expression cassette and the recombinant expression cassette is introduced into insect cells either by transfection of the cells directly or with a transplacement vector comprising the expression cassette and wild-type baculovirus DNA or by infection of the cells with a recombinant baculovirus comprising the expression cassette. Preferably the insect cellular promoter allows expression at an early stage of infection and/or it allows expression in substantially all tissues of an insect. In a preferred embodiment, the "insect cellular promoter" is a promoter which does not normally direct the expression of the heterologous structural gene and is not naturally functionally attached to that structural gene. For example, if the heterologous structural gene is a gene naturally present in the insect genome, the insect cellular promoter is not the promoter which normally directs the expression of the heterologous structural gene in the wild-type insect. In one embodiment, the insect cellular promoter is an insect cytoplasmic actin promoter, most preferably, the insect cellular promoter is the cytoplasmic actin promoter of *B. mori*. In another embodiment, the insect cellular promoter comprises the promoter for an insect ribosomal gene, tRNA gene, histone gene, or tubulin gene.

The term "enhancer" means a nucleic acid sequence that increases the frequency with which transcription initiates from a promoter functionally linked to the enhancer. The enhancer can function in any location, either upstream or downstream, relative to the promoter. The enhancer in this invention is any DNA sequence which is capable of increasing the level of transcription from the insect cellular promoter when the enhancer is functionally linked to the promoter. One skilled in the art, given the present disclosure, could readily determine whether a particular DNA fragment functioned as an enhancer by inserting the fragment next to the cellular promoter and measuring the level of production of mRNA from the promoter. In a preferred embodiment the enhancer is the 1.2 kb DNA fragment shown in FIG. 9. More preferably, the enhancer is that region of the 1.2 kb BmNPV enhancer fragment which potentiates the transcription from the cellular promoter. One skilled in the art given the disclosure of this invention could readily determine the size of fragment from the 1.2 kb DNA fragment shown in FIG. 9 which potentiates the transcription from the cellular promoter by inserting fragments of differing sizes from that DNA fragment into an expression cassette of the present invention and determining by the methods of this invention whether increased production of a heterologous protein was achieved.

Preferably, the level of transcription is enhanced from the cellular promoter by the enhancer when transcription is increased by a level of at least about 10 fold, more preferably the level of transcription is increased by a level of at least about 100 fold.

In order to enhance the efficiency of the expression of the heterologous gene, it is contemplated that the insect cellular promoter may be genetically modified so as to make it capable of expressing the heterologous gene more efficiently in the cells of the insect brain, gut and/or muscle. In addition, it is contemplated that the enhancer may also be genetically modified to further enhance expression. In addition, the use of a tissue-specific "enhancer" element or some other DNA sequence is contemplated such that, while the promoter is expressed in substantially all tissues, it is over-expressed in certain tissues of the insect.

It is further contemplated that the expression cassette will include a DNA fragment encoding a signal peptide sequence functionally linked to the heterologous gene for the purposes of directing secretion of the heterologous protein out of the insect cell. In this case, the signal sequence must be linked in frame with the open reading frame of the heterologous gene.

The term "functionally linked" or "functionally attached" when describing the relationship between two DNA regions simply means that they are functionally related to each other and they are located on the same nucleic acid fragment. A promoter is functionally attached to a structural gene if it controls the transcription of the gene and it is located on the same nucleic acid fragment as the gene. An enhancer is functionally linked to a structural gene if it enhances the transcription of that gene and it is functionally located on the same nucleic acid fragment as the gene.

The term "IE-1 gene" refers to the IE-1 gene from a baculovirus genome. (Huybrechts et al., 1992) In one embodiment, the IE-1 gene is obtained from the BmNPV genome. In another embodiment, the IE-1 gene is obtained from the AcNPV genome.

The term "constitutive expression" means that the promoter is expressed continuously in the insect cells. In the case of insect cells into which recombinant virus has been introduced, the promoter is expressed for at least 20 hours after introduction, more preferably for at least 30 hours after introduction and most preferably at least 60 hours after introduction.

The term "at an early stage of introduction" means production of the heterologous protein under the functional control of the insect cellular promoter occurs before expression would occur if the heterologous protein was functionally attached to a polyhedron promoter or to other viral promoters that are functional after viral DNA replication. Where insect tissue culture cells are infected with recombinant virus, expression occurs at an early stage of introduction where the heterologous protein is produced before about 10 hours, more preferably before about 8 hours, most preferably before about 5 hours post infection. Where insect larvae are infected with recombinant virus containing the expression cassette, expression will occur at an early stage of introduction when it occurs before about 48 hours post infection, more preferably before 24 hours post infection and most preferably before 12 hrs post infection.

The term "in substantially all insect tissues" means that the heterologous protein is expressed in all insect tissues, more preferably the gut, brain, nervous system, fat body and muscle tissue, into which it is introduced by infection with a recombinant baculovirus comprising a structural gene coding for the heterologous protein functionally linked to an insect cellular promoter.

The terms "producing heterologous protein" or "expressing heterologous protein" means that the structural gene encoding the heterologous protein is transcribed into mRNA and that the mRNA is further translated into protein. In a preferred embodiment the heterologous protein will be properly processed by the insect cell, although such processing may be in a tissue specific manner.

The term "structural gene" refers to those DNA sequences which, when functionally attached to a cellular promoter, will be transcribed and produce a heterologous protein in insect cells.

The term "heterologous structural gene" or "heterologous gene" is a structural gene which is not normally present in wild-type baculovirus genomes, but which may or may not be present in insect genomes. In a preferred embodiment the heterologous structural gene does not include the structural gene which is functionally attached to the insect cellular promoter in wild-type insect cells. A heterologous structural gene is a structural gene which will be transcribed and will produce a protein when functionally attached to an insect cellular promoter in a recombinant expression cassette or to an enhancer and promoter in a recombinant enhanced expression cassette and thereafter introduced into cells of an insect either by infection of cells by a recombinant baculovirus containing the cassette or by transfection of cells with a transplacement fragment containing the cassette or with the recombinant expression cassette alone. While the chloramphenicol acetyltransferase ("CAT") gene was used to characterize the expression of the heterologous protein under the control of the cellular promoter in the examples provided herein, it will be recognized that any heterologous structural gene meeting the above criteria may be used in the invention.

The term "heterologous protein" refers to a protein encoded by a heterologous structural gene and which is not normally expressed by the baculovirus, but which may be expressed by insect cells in a regulated manner. The protein may be compatible or incompatible with the insect. Examples of compatible heterologous proteins are chloramphenicol acetyltransferase, human alpha interferon (IFN-α), insulin-like growth factor-II (IGF-II), human interleukin 3, mouse interleukin 3, human and mouse interleukin 4, human T-lymphotropic virus (HTLV-1) p40$^x$, HTLV-1 env, human immunodeficiency virus (HIV-1) gag, pol, sor, gp41, and gp120, adenovirus Ela, Japanese encephalitis virus env (N), bovine papillomavirus 1 (BPV1) E2, HPV6b E2, BPV1 E6, and human apolipoproteins A and E; β-galactosidase, hepatitis B surface antigen, HIV-1 env, HIV-1 gag, HTLV-1 p40$^x$, human IFN-β, human interleukin 2, c-myc, *D. melanogaster* Kruppel gene product, bluetongue virus VP2 and VP3, human parainfluenza virus hemagglutinin (HA), influenza polymerases PA, PB1, and PB2, influenza virus HA, lymphocytic choriomeningitis virus (LCMV) GPC and N proteins, *Neurospora crassa* activator protein, polyomavirus T antigen, simian virus 40 (SV40) small t antigen, SV40 large T antigen, Punta Toro phlebovirus N and Ns proteins, simian rotavirus VP6, CD4 (T4), human erythropoietin, Hantaan virus structural protein, human epidermal growth factor (EGF) receptor, human insulin receptor, human B lymphotrophic virus 130-kd protein, hepatitis A virus VP1, human tyrosine hydroxylase, human glucocerebrosidase, and mouse p53.

The term "incompatible protein" means either a toxic protein or an insect incapacitating protein of insect or non-insect origin whose unregulated expression could incapacitate the insect through unbalancing of an important physiological process. An incompatible protein will enhance the inactivation of the insect by the baculovirus.

The term "toxic gene" means a heterologous DNA sequence which encodes for a heterologous protein product that inactivates the larvae or which results in extensive tissue damage to the larvae and eventually death. Suitable toxic genes include genes that encode insect specific toxins or other gene products which, when inserted into the expression cassette improve the ability of the baculovirus to paralyze or kill the insect. Such toxic genes include genes which encode for endotoxins from *Bacillus thuringiensis*. There are *B. thuringiensis* strains with activities against a wide range of insect species. Many strains produce a toxin that is active against lepidopteran larvae. Some strains produce toxins that affect dipteran or coleopteran larvae. Other suitable toxic genes include genes encoding: an insect specific neurotoxin, AaIT, from the venom of the North African (Algerian) Scorpion, *Androctonus australis* Hector (Stewart et al., 1991); Tox-34, which encodes TxP-1 toxin associated with the mite *Pyemotes tritici*. (Tomalski and Miller, 1991); the depressant insect toxin BjIT2 of the scorpion *Buthotus judaicus* (Zilberg, N., et al., 1991, *Toxicon,* 29:1155–1158); an alpha insect toxin from the scorpion *Leirus quinquestriatus hebraeus* (Gurevitz, M., et al., 1991, *Toxicon,* 29:1270–1272); and insect paralytic peptides (Skinner W., et al., 1991, *J. Biol. Chem.,* 20:12873–12877).

The term "incapacitating protein" means a protein whose unregulated expression could incapacitate the insect through unbalancing of an important physiological process. Examples of incapacitating genes include: insect or non-insect neuropeptides such as FMRFamide-related peptides, enkephalin-related peptides, tachykinins, adipokinetic hormones, other myotropic peptides, such as proctolin, leucokinins, achetakinins, drosulfakinins, locustakinin, locustamyotropins, leucopyrokinin, locustapyrokinin, leucosulfakinin, locustasulfakinin, allatostatins, allatotropin, alkaline phosphatases, collagenases, chitinases, juvenile hormone esterases and epoxide hydrolases, ecdysone and juvenile hormone receptors, eclosion hormone, prothoracicotropic hormone and the synthetic diuretic hormone gene of *M. sexta.*

The term "introduction" refers to either infection or transfection of insect cells.

Insects are "incapacitated" when substantially all of the insects are killed. In a preferred embodiment at least about 50% of the insects are killed, more preferably at least about 75% of the insects are killed.

The term "infection" refers to the invasion by pathogenic viral agents of cells where conditions are favorable for their replication and growth. Such invasion can be by placing the viral particles directly on the insect cell culture or by injection of the insect larvae with the recombinant virus or by oral ingestion of the viral particles by the insect. The amount of recombinant virus injected into the larvae will be from $10^2$ to $10^5$ pfu of non-occluded virus/larvae. Alternatively, larvae can be infected by the oral route using occlusion bodies carrying recombinant viruses. In general, the amount of occlusion bodies fed to the larvae is that amount which corresponds to the $LD_{50}$ for that species of baculovirus and insect host. The $LD_50$ varies with each species of baculovirus and the age of the larvae. One skilled in the art can readily determine the amount of occlusion bodies to be administered. Typically, the amount will vary from 10–$10^6$ occlusion bodies/insect.

In those vectors in which the polyhedron gene has been replaced by the expression cassette, the recombinant virus does not produce the polyhedron protein, and occlusion body formation does not occur. However, co-infection of cell cultures with the budded virus forms of both recombinant and wild-type viruses provides occlusion bodies containing both recombinant and wild-type viruses. This mixture of both recombinant and wild-type viruses in occlusion bodies bay be used for infection of insect larvae by the oral route. Alternatively, by constructing different transplacement vectors, it is possible to insert the recombinant expression cassette in other sites of the viral genome to generate occluded recombinant baculoviruses.

The term "transfection" refers to a technique for introducing purified nucleic acids into cells. Calcium phosphate or other appropriate agents such as dextran sulfate are added to the DNA solution and the solution is placed on the insect cells. The insect cells will take up the DNA precipitated by the addition of calcium phosphate or other agents such as dextran sulphate to a DNA solution. Alternatively, DNA can be introduced into the cells by electroporation. In a preferred embodiment, the DNA is introduced into the cells by mixing the DNA solution with "Lipofectin" (GIBCO BRL Canada, Burlington, Ontario) and adding the mixture to the cells.

Once an appropriate transplacement fragment or transplacement vector containing the heterologous gene is constructed, host insect cells are transfected simultaneously with wild-type viral DNA and the transplacement fragment or vector DNA containing baculovirus DNA sequences homologous to the wild-type viral DNA. The genetic recombination system of the host insect cell recombines the plasmid and viral DNAs. Double crossover recombination events at homologous DNA sites results in the replacement of sequences of the viral genome with a portion of the transplacement fragment DNA, thereby inserting the recombinant expression cassette DNA containing the heterologous gene into the preferred site of the viral genome. Where the transplacement fragment or vector contains DNA sequences from the viral polyhedron gene, a double recombination/ cross-over event between the homologous viral sequences in the transplacement fragment and the wild-type baculovirus genome will result in the expression cassette replacing a portion of the polyhedron gene of the wild-type genome. Following amplification of serially diluted progeny viruses, recombinant viruses are selected by hybridization to heterologous gene probes and confirmed by restriction endonuclease and DNA sequence analysis identification techniques. In the case of polyhedron substitution expression systems, cells containing recombinant viruses with double crossovers can be also identified visually because they do not contain viral occlusion bodies.

The term "insect cells" means insect cells from the insect species which are subject to baculovirus infection. For example: *Autographa californica; Bombyx mori; Spodoptera frugiperda; Choristoneura fumiferana; Heliothis virescens; Heliothis zea; Orgyia pseudotsugata; Lymantria dispar; Plutella xylostella; Malacostoma disstria; Trichoplusia ni; Pieris rapae; Mamestra configurata; Hyalophora cecropia.*

Methodology

In view of the fact that ferocious feeding is the major destructive activity of most lepidopteran pests, recombinant baculoviruses that effect an immediate incapacitation of pests by early expression of the incapacitating genes in the cells of the midgut would be advantageous. It has now been discovered that there are genetic elements which potentiate activity of an insect cellular promoter functionally attached to a structural gene for a heterologous protein. Further, the protein is expressed early in the baculovirus infection cycle and in substantially all infected tissues of the insect including the gut. Therefore, if a heterologous gene whose product incapacitates the insect is placed under the control of an insect cellular promoter in a recombinant baculovirus, the gene product will be expressed in substantially all infected tissues of the insect at an early stage of infection and thus rapidly inactivate the insect.

The first genetic element is an enhancer which can stimulate the cellular promoter upon covalent linkage to the promoter. The second genetic element is a structural gene, IE-1, of the baculovirus genome which is expressed at the early stages of infection under the control of the transcriptional machinery of the cell. It has been found that this gene encodes a protein which acts as a transcriptional regulator Upon expression, this protein stimulates the level of expression of the cellular promoter of the recombinant expression cassette. This stimulation occurs in trans. i.e. the enhancing effect is the same irrespective of whether the gene encoding IE-1 is physically linked to the cellular promoter of the expression cassette in a vector or not.

The present invention is directed, in part, to the discovery of an enhanced expression cassette which can be used to generate recombinant baculoviruses that can express heterologous proteins under the control of an insect cellular promoter and an enhancer in substantially all tissues of the insect.

An enhanced expression cassette may be constructed which contains an insect cellular promoter, an enhancer and a termination sequence. The cassette also contains a polylinker sequence comprising a number of unique restriction sites into which the desired structural gene encoding a heterologous protein may be inserted. Preferably the enhanced expression cassette comprises the plasmid pBmeA. The desired heterologous gene may be inserted into the expression cassette such that the structural gene is functionally linked to the insect cellular promoter and the enhancer.

Another vector may also be constructed which contains a portion of the baculovirus that can sustain insertions of non-viral DNA fragments. The recombinant enhanced expression cassette containing the heterologous gene may be excised from the first vector and inserted into a nucleotide site in the baculovirus sequence present on the other vector, thereby creating a transplacement vector. The recombinant expression cassette or the transplacement vector may each be transfected into insect cells for expression of the heterologous protein. The transplacement vector may also be co-transfected into insect tissue culture cells with wild-type baculovirus DNA which is comprises a DNA fragment homologous to the portion of baculovirus DNA present on the transplacement vector. Recombinant baculovirus genomes containing the expression cassette may then be generated by double cross-over events. Such recombinant viruses can be used to infect insect cells for the purposes of incapacitating the insects.

If a continuous high level expression of foreign genes is desired in insect lines, cells may be transformed with enhanced recombinant expression cassettes employing cellular promoters and enhancers functionally linked to the foreign gene. To achieve continuous high level of expression of foreign genes, in one embodiment, normal insect tissue culture cells can be transformed with a plasmid containing an enhanced expression cassette comprising a cellular promoter and an enhancer functionally linked to a heterologous gene and an extra gene expressing a selective marker (e.g. antibiotic resistance gene under the control of a promoter that functions constitutively in insect cells). Application of a relevant selection should lead to integration of one or more multiple copies of the plasmid into the chromosomes of the cells, thus generating an insect cell line capable of continuous high level expression of the foreign gene present in the recombinant expression cassette. The level of transcription from the cellular promoter functionally linked to an enhancer as compared to the level of transcription from the cellular promoter alone is preferably at least about 10 fold and more preferably at least about 100 fold.

The selective marker gene can be any gene which codes for a protein, wherein cells producing this protein can be positively selected from the general population. The type of selectable marker is not critical so long as cells having the marker may be selected. Selectable markers useful in the present invention are antibiotic resistance genes, for example the neomycin gene, the hygromycin gene and the dihydrofolate reductase gene (DHFR).

In another embodiment the insect cells can be transformed with a vector containing the IE-1 gene and a suitable resistance/selectable marker gene. Application of a relevant selection should lead to integration of one or more multiple copies of the vector into the chromosomes of the cells, thus generating an insect cell line capable of continuous high level expression of the IE-1 gene product. Thus the cell line will contain the IE-1 gene in the absence of added baculovirus. Such a cell line can be subsequently transformed with additional vectors containing either the recombinant expression cassette containing an insect cellular promoter functionally linked to a heterologous gene or the enhanced recombinant expression cassette containing an enhancer and an insect cellular promoter functionally linked to a heterologous gene. The method of creating expression vectors containing insect cellular promoters is described in U.S. patent application Ser. No. 07/904,408 which is incorporated by reference herein in its entirety. The second vector may also comprise an additional gene conferring resistance to a second selection agent. In both cases, synthesis of the foreign protein will be continuous, because integrated expression cassettes cannot be lost through replication and the insect cells never die because they are not infected by any viruses. Expression will also occur at a high level. The level of production of heterologous proteins in cells expressing the IE-1 gene as compared to cells without the IE-1 gene is preferably at least about 10 fold greater and more preferably at least about 100 fold greater. The production of heterologous proteins in cells expressing the IE-1 gene where the heterologous gene is functionally linked to an enhancer is preferably at least about 100 fold greater and more preferably at least about 1000 fold greater than in cells lacking both the IE-1 protein and the enhancer.

In one embodiment, the desired heterologous protein is the chloramphenicol acetyltransferase structural gene sequence (CAT). This gene, cat, was inserted into the BamHI site of pBmA to create pBmA.cat. In another embodiment a fragment containing the sequence for *Heliothis virescens* juvenile hormone esterase cDNA (Hanzlik et al., 1990) is inserted into the EcoRI site of the polylinker of plasmid pBmA. In another embodiment a fragment containing the sequence for bovine preproenkephalin cDNA (Gubler and Hoffman, 1983) is inserted between the EcoRI and BamHI sites of the polylinker of plasmid pBmA. In another embodiment a fragment containing the gene for Drosophila FMRFamide-like peptide precursor (Schneider and Taghert, 1990) is ligated into the EcoRI site of the polylinker of plasmid pBmA. In other embodiments the genes for the neuropeptide proctolin, mouse tissue nonspecific alkaline phosphatase, chicken protamine gene, *Pyemotes tritici* insectotoxin PxP-1 and *Androctonus australis* insectotoxin AaIT will also be inserted into the expression cassette.

If the development of recombinant baculoviruses for use as insect pest control agents is desired, the enhancer is inserted into the expression cassette containing the insect cellular promoter. An incapacitating gene ins then placed under the control of the insect cellular promoter and the enhancer. A recombinant baculovirus in the form of an occlusion body is created to contain the enhanced recombinant expression cassette by the methods of this invention. Insects may then be infected with the recombinant baculovirus in the form of an occlusion body. In the case of recombinant baculoviruses a plasmid containing the IE-1 gene is not required since the IE-1 gene is produced in the infected cells by the baculovirus' genome immediately upon infection. In the case of recombinant baculoviruses, the level of enhancement, relative to recombinant viruses without enhancers will preferably be at least about 10 fold, more preferably at least about 100 fold.

Using the methods described in this invention, a person skilled in the art can construct an recombinant expression cassette containing an insect cellular promoter and an enhancer able to direct the expression of any desired heterologous protein such that when the recombinant expression cassette is introduced into insect cells the heterologous protein will be expressed at an increased level in substantially all of the insect tissues at an early stage in the infection. It is also obvious that the invention can be applied to any available insects that are subject to baculovirus infection.

The following examples are offered to illustrate the present invention and should not be construed in any way as limiting the scope of this invention.

EXAMPLES

Chemicals used in the following examples were obtained from the following companies:

Amersham Canada Ltd., Oakville, Ontario, Canada
J. T. Baker, Phillipsburg, N.J.
BioRad Laboratories Ltd. Canada, Mississauga, Ontario, Canada
Boehringer Mannheim, Laval, Quebec, Canada
GIBCO BRL Canada, Burlington, Ontario, Canada
Hyclone Laboratories, Inc., Logan, Utah
JRH Biosciences, Inc., Lenexa, Kans.
New England Biolabs, Inc., Mississauga, Ontario, Canada
Pharmacia LKB, Baie d' Urfe', Quebec, Canada
Promega Corporation, Madison, Wis.
Sigma, St. Louis, Mo.
Stratagene, La Jolla, Calif.
United States Biochemicals, Cleveland, Ohio All enzymes used for the construction and characterization of the recombinant plasmids and baculoviruses were obtained from Pharmacia, LKB; New England Biolabs, Inc.; GIBCO BRL Canada; Boehinger Mannheim; and used according to those suppliers recommendations. The cloning procedures set forth in the examples are standard methods described in Sambrook et al., *Molecular Cloning: A Laboratory Manual*, Cold Spring Harbor Laboratory (1982) which is incorporated herein by reference. This reference includes procedures for the following standard methods: cloning procedures with *E. coli* plasmids, transformation of *E. coli* cells; plasmid DNA purification, agarose gel electrophoresis, restriction endonuclease digestion, ligation of DNA fragments and other DNA-modifying enzyme reactions.

Example 1
Plasmid Constructions

The vector, pBmA (FIG. 1A), is a pBluescript (Stratagene) derivative of clone pA3-5500 which contains the A3 cytoplasmic actin gene of *Bombyx mori* (Mounier and Prudhomme, 1986). Plasmid pBmA was constructed to contain 1.5 kb of the A3 gene 5' flanking sequences and part of its first exon to position +67 (relative to transcription initiation), a polylinker region derived from plasmid pBluescript (Stratagene) for insertion of foreign gene sequences, and an additional 1.05 kb of the A3 gene sequences encompassing part of the third exon of the gene from position +836 and adjacent 3' flanking sequences which contain signals required for RNA transcript polyadenylation. This expression vector was constructed by (1) subcloning into plasmid Bluescript SK+ (Stratagene) a 1.5 kb Kpnl/AccI fragment of clone pA3-5500 containing the 5' flanking, 5' untranslated and coding sequences of the A3 gene up to position +67 to generate plasmid pBmAp; (2) mutagenizing the ATG translation initiation codon present at position +36 to +38 of the actin coding sequence in plasmid pBmAp into AGG, AAG or ACG by the method of Kunkel (1985) to generate plasmids pBmAp.AGG, pBmAp.AAG and pBmAp.ACG; (3) subcloning into plasmid pSP72 (Promega Corporation) a 1.05 kb XhoI/SalI fragment of clone pA3-5500, containing part of the third exon of the actin gene from position +836 and adjacent 3' flanking sequences which include signals required for RNA transcript polyadenylation, to generate plasmid pBmAt; (4) converting the unique XhoI site of plasmid pBmAt into a NotI site by digestion of this plasmid with XhoI (GIBCO BRL), end-filling with Klenow DNA polymerase (Boehringer Mannheim), ligation of NotI linkers (DNA Synthesis Laboratory, University of Calgary) with DNA ligase (New England Biolabs, Inc.), digestion with NotI (New England Biolabs, Inc.) and religation with T4 DNA ligase (Boehringer Mannheim) to generate plasmid pBmAtN; (5) isolating the actin insert fragment from plasmid pBmAtN by double digestion with NotI and SacII (New England Biolabs, Inc.) and electroelution following separation on an agarose gel; (6) ligating the NotI/SacII actin fragment from (5) above into NotI/SacII-digested plasmids pBmAp.AGG, pBmAp.AAG and pBmAp.ACG with T4 DNA ligase to generate the actin expression cassettes pBmAo.AGG, pBmAo.AAG and pBmAo.ACG. The actin expression cassette pBmA (FIG. 1A) was derived from plasmid pBmAo.AGG by digestion with SalI (complete digestion) and BamHI (partial digestion) to remove part of the polylinker sequence of plasmid pSP72 present at the 3' terminus of the actin insert, and religation with T4 DNA ligase. Translation initiation from any gene inserted in the pBmA actin expression cassette polylinker (FIG. 1A) occurs from the first ATG triplet of the insert.

A 900 bp XhoII fragment containing the chloramphenicol acetyl transferase (CAT) open-reading frame was excised from pCARCAT-1 (Mitsialis et al., 1987) by digestion of the DNA with the restriction enzyme XhoII. This fragment includes the entire coding information of CAT, all of the 5' and most of the 3'-untranslated gene sequences, as well as 63 bp of the 5' untranslated region of the early transcription unit of SV40. It should be emphasized that the SV40 sequences are completely devoid of any promoter or enhancer elements. Therefore, the transcripts must depend on control elements contributed by the actin promoter sequences. This fragment was inserted into the BamHI site of pBmA to create pBmA.cat (FIG. 1B).

To produce an appropriate viral transplacement vector plasmid pBmp2, which contains a copy of the BmNPV polyhedron gene, whose promoter and part of the coding sequences have been deleted, was created (Iatrou and Meidinger, 1989). Initially plasmid Bmp/pP3 was constructed as described in Iatrou et al. (1985). More specifically, the B. mori baculovirus genome was digested with PstI, a 10 kb PstI fragment containing the polyhedron gene was identified by Southern blot hybridization using $^{32}$P-labelled polyhedron gene sequences of AcNPV, purified by electroelution following agarose gel electrophoresis and cloned into the PstI site of pUC9. Bal 31 deletion mutagenesis was accomplished by linearizing plasmid Bmp/pP3 DNA at a unique XbaI site located 194 bp downstream of the 5' terminus of the polyhedron gene (nt 147 of the protein-coding sequence between codons 49 and 50; see Iatrou et al. (1985) for sequence details) and incubating with exonuclease Bal 31 in a reaction containing 0.6 M NaCl, 12.5 mM CaCl$_2$, 12.5 mM MgCl$_2$, 20 mM Tris-HCl, pH 7.8, 160 µg/ml linearized plasmid DNA and 75 units/ml of Bal 31 (New England Biolabs, Inc.) at 30° C. Aliquots were withdrawn at 10 min. and at 3 min. intervals thereafter, up to a total of 25 minutes, and flushed into a tube containing two reaction volumes of 50 mM EDTA and two volumes of water-saturated phenol. Following purification by phenol extraction, combined aliquots were 3' end-filled with Klenow DNA polymerase, as described (Iatrou et al., 1985). XbaI linkers were ligated to the end-filled DNA in a reaction containing 66 mM Tris-HCl, pH 7.5, 66 µM ATP, 6.6 mM MgCl$_2$, 10 mM DTT, 0.125 µg/ml of XbaI linkers, 4 µg/ml of end-filled DNA and 300 units/ml T4 DNA ligase (Pharmacia LKB). Linker-ligated DNA was purified by electroelution, restricted with XbaI, and circularized by incubating in the above reaction mix at a DNA concentration of 0.4 µg/ml with 30 units/ml T4 DNA ligase. Transformation of circularized plasmid DNA into Escherichia coli HB101 resulted in the generation of a library of clones containing polyhedron genes with segmental deletions of various lengths starting from the unique XbaI site of the gene. Plasmid DNA from several clones was characterized by sequence analysis (Maxam and Gilbert, 1977) and plasmid pBmp2 which has the region from nt-90 to nt 339 of the polyhedron gene deleted was selected as the recipient for insertion of the actin expression cassette.

Plasmid pBmp2 was digested with XbaI and the XbaI site converted to an SstI site by the addition of linkers and religation. The resulting plasmid was designated pBmp2s (FIG. 1C).

The SstI fragment containing the A3 promoter-CAT structural gene DNA fragment was removed from pBmA.cat by digestion with SstI and then inserted into the SstI site of pBmp2s to create pBmp2s/A.cat (FIG. 1D). A recombinant virus, BmNPV/A.cat was obtained using this transfer vector as described in Example 2.

Plasmid pBmp26.cat (FIG. 1E) contains a mutated polyhedron gene promoter directing the expression of the cat structural gene. It has been constructed by subcloning the cat structural gene into plasmid pBmp26T. Plasmid pBmp26T is a derivative of plasmid pBmp26 which was initially selected from the library of clones generated by Bal 31 deletion mutagenesis of the polyhedron gene described above for plasmid pBmp2, and shown by DNA sequence analysis to encompass a deletion of nucleotides +27 to +251 (relative to translation initiation) of the polyhedron gene. The polyhedron gene translation initiation codon ATG was removed from plasmid pBmp26 containing the deleted polyhedron gene, on a 2.0 kb XhoI/XbaI fragment and mutationally converted into ATT by the method of Kunkel (1985). The mutated 2.0 kb fragment was then cloned into XhoI/XbaI digested Bmp/pP14 to create pBmp26T. Plasmid Bmp/pP14 was created in the same manner as Bmp/pP3 described above (Iatrou et al., 1985), but contains the baculoviral sequences in the opposite orientation. As a result, pBmp26T has a deletion from +27 to +146 with ATT instead of ATG. Plasmid pBmp26T was then digested with XbaI and the 900 bp XhoII CAT structural gene open-reading frame was inserted into the plasmid by blunt end ligation to create pBmp26.cat. The polyhedron promoter sequences are retained in this plasmid and direct the transcription of the cat structural gene.

Example 2

Cell Culture and Viruses Bombyx mori Bm5 silkworm tissue culture cells (Grace, 1967) were maintained in IPL-41 medium (JRH Biosciences, Inc.) containing 10% fetal calf serum (Hyclone Laboratories, Inc.), as previously described (Iatrou et al., 1985). Recombinant viruses were obtained by co-transfection of Bm5 cells with pBmp2s/A.cat DNA or pBmp26.cat DNA and wild-type BmNPV DNA. Bm5 cells were transfected in 6-well microtiter plates in a manner similar to that described by Iatrou and Meidinger (1989). Typically, Bm5 cells were plated in 10 cm$^2$ plates or microtiter wells at a density of 2×10 cells/cm$^2$. Transfection was accomplished by removing the culture medium, rinsing the cell monolayer with basal medium (no fetal calf serum) and adding 500 $\mu$ of transfection solution [30 $\mu$g/ml "Lipofectin" (GIBCO BRL Canada) in basal IPL-41 (JRH Biosciences, Inc.) containing 5 $\mu$g/ml of the transfer vector DNA and 0.2 $\mu$g/ml BmNPV DNA]. After incubation for 5 hours, the transfection solution was removed, the cells rinsed with basal medium and 2 ml of complete medium containing 50 $\mu$g/ml of gentamicin was added. A purified recombinant virus was obtained by serial dilution as described previously (Pen et al., 1989; Goswami and Glazer, 1991) and its structure confirmed by Southern hybridization with $^{32}$P-labelled 900 bp XhoII cat gene fragment and nucleotide sequence analysis (Maxam and Gilbert, 1977).

The purified virus was propagated by infecting Bm5 cells grown in 25 cm$^2$ flasks at a density of 1×10$^6$ cells/ml. The medium from the infected cells, containing recombinant virus, was collected 4 to 7 days post infection and used as inoculum for subsequent experiments.

Example 3

Infections

A. Bm5 cells to be infected with virus were seeded into 24-well microliter plates at a density of 2×10$^5$ cells (in 500 $\mu$l medium) per well. After 3 days, 100 $\mu$l of viral inoculum [10$^6$ plaque forming units (pfu)] obtained by the method of Example 2, was added to each well. Time after infection was counted from the time that the virus was added to the medium. Cells were removed from the wells at the appropriate time by repeated pipeting.

Cells were pelleted from the medium at 3000×g for 5 min, suspended in 1 ml PBS (10 mM KH$_2$PO$_4$, 2 mM NaH$_2$PO$_4$, 140 mM NaCl, 40 mM KCl) and repelleted. The cells were then resuspended in 200 $\mu$l of 0.25 M Tris-HCl, pH 7.8, freeze-thawed three times using dry ice to disrupt the cells and, after centrifugation, the supernatants retained for CAT assays.

B. Silkworm larvae were reared on a diet of fresh mulberry leaves, and were injected with virus at the beginning of the 5th instar. After incubating the animals at 0° C. for 1 hour, 10 $\mu$l of viral inoculum (10$^5$ pfu) obtained by the method of Example 2 was injected into the haemocoel using a 26 gauge needle. The infected animals were maintained as before and collected at the appropriate time for dissection.

Larvae were dissected in cold PBS and the appropriate tissues were removed. Midguts were cut open longitudinally to allow removal of the gut contents and all tissues were rinsed extensively with several changes of PBS. The tissue samples were ground in 0.25 M Tris-HCl, pH 7.8 with a small pestle in a microcentrifuge tube, freeze-thawed and centrifuged as described about. All larval extracts were heated to 65° C. for 5 minutes to inactivate cellular deacetylase activities before use in CAT assays.

Example 4

Protein and CAT Assays

Assays for protein content and CAT activity of the extracts from transfected and infected cells and infected larvae were performed as follows. For CAT assays, cells (usually 2×10$^5$ to 2×10$^6$ on plating day) were collected 24 hours post-transfection or 48 hours post-infection and rinsed with PBS (10 mM KH$_2$PO$_4$, 2 mM NaH$_2$PO$_4$, 140 mM NaCl, and 40 mM KCl). After pelleting at 3000×g for 5 minutes, the cells were resuspended in 100 $\mu$l of 0.25 mM Tris-HCl, pH 7.8 and the suspension was freeze-thawed in dry ice 3 times to disrupt the cells. After centrifugation, the protein content of the supernatant was determined by the Bradford protein assay (Bradford, 1976) using BioRad Laboratories Ltd. Canada protein assay reagent and bovine serum albumin as the standard. Samples were assayed for CAT activity (Gorman et al., 1982) in 150 Al total reaction volumes containing 0.25 M Tris-HCl, pH 7.8, 0.5 mM acetyl-CoA (Sigma), 2.4 nmol [$^{14}$C]-chloramphenicol (50 mCi/nmol; Amersham Canada Ltd.). After 1 hour of incubation at 37° C., the reactions were extracted with 500 $\mu$l of ethyl acetate and dried. The resulting residues were resuspended in 15 $\mu$l of ethyl acetate and spotted onto silica-gel thin-layer chromatography plates (J. T. Baker). The plates were developed for 2 hours in a 95:5 chloroform-methanol solvent mixture, after which they were dried and autoradiographed. In some instances, the areas of the reaction products (the acetylated forms and the residual starting material) were cut out of the plates and quantitated by liquid scintillation counting. One unit of CAT activity catalyzes the acetylation of one nanomole of chloramphenicol per minute at 37° C.

Example 5

Presence of CAT Activity in Recombinant Viruses

It was necessary to determine whether the infected cells would contain any background level of CAT activity as a result of the extremely stable CAT protein being encapsulated within the recombinant non- occluded virus (NOV) and released within the cell immediately upon infection. Non-occluded virus (NOV) was isolated from the medium by centrifugation at 50,000 rpm in a Beckman 100.2 rotor for 1 hour. After removal of the supernatant, the viral pellet was rinsed with 1 ml H$_2$O, resuspended in 1.6 ml H$_2$0 and recentrifuged as before. The final pellet was again rinsed and resuspended in H$_2$O. 20 $\mu$l of isolated non-occluded virus or medium containing NOV was assayed for 1 hour as described in Example 4. The results are shown in FIG. 2. The upper spot (Ac-C) represent acetyl chloramphenicol, the products of the CAT reaction, while the lower spot in each assay (C) represents the substrate, chloramphenicol. Medium, collected from infected cells 5 days after infection and used as inoculum, was found to contain high levels of CAT activity (FIG. 2A, right). Non-occluded virus (NOV) isolated from the medium was lysed by sonication and was also found to contain a significant amount of CAT activity even after extensive washing (FIG. 2A, left).

Bm5 cells were infected with BmNPV/A.cat or BmNPV/ P26.cat inoculum obtained by the method of Example 2. The cells were assayed for CAT activity by the method of Example 4. Cells infected with either recombinant virus were found to contain background CAT activity 5 minutes after addition of the viral inoculum. The level of CAT activity in these cells reached a plateau within 20 minutes (FIG. 2B) and this level was maintained for several hours.

Bm5 cells were infected with BmNPV/A.cat or BmNPV/ P26.cat inoculum of Example 2 containing medium and virus, or with NOV isolated by the method described in this example or were mock inoculated. The cells were collected 1 hour after infection and were washed once (1×) or five (5×) times with 1 ml PBS. When cells were infected with the standard inoculum, which contained both virus and medium, a portion of this CAT activity could be removed by washing the cells with PBS, but a significant fraction remained even after extensive washing. When cells were infected with isolated virus, none of the activity could be removed by washing (FIG. 2C). It was concluded, therefore, that this remaining activity represented CAT enzyme attached to or introduced into the cells during viral infection, and that this background value would have to be subtracted from all subsequent measurements in order to quantitate the amount of CAT enzyme present due to promoter activity during time course experiments.

Example 6
Time Course of Gene Expression in Bm5 Cells

Bm5 cells were infected with recombinant virus BmNPV/A.cat or BmNPV/P26.cat by the methods of Example 3 and cell extracts were assayed for CAT activity at various times after infection. The CAT assays were performed using 5 μg cell protein incubated for 1 hour from cells infected with BmNPV/A.cat and 1 μg cell protein for 1 hour from cells infected with BmNPV/P26.cat by the method described in Example 4.

Figure 3B:
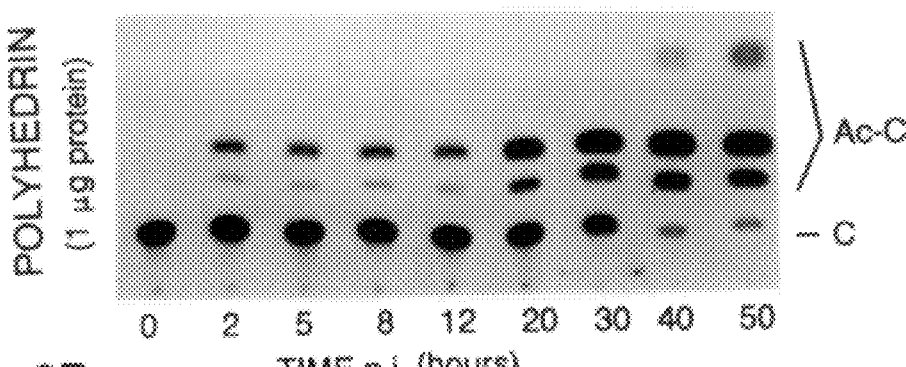
Figure 3C:
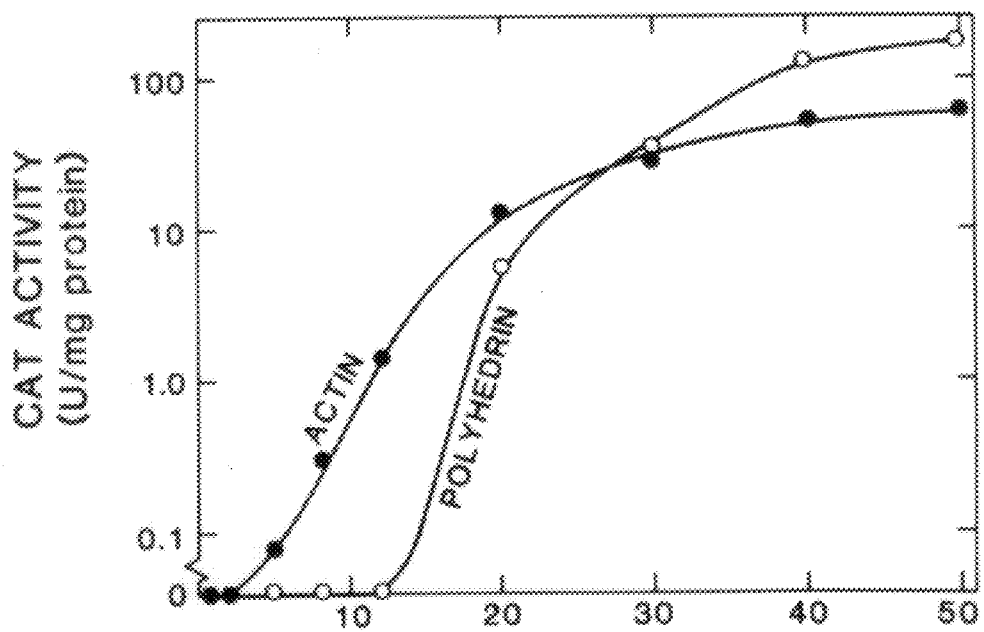

CAT activity above the background level, determined by the method of Example 5, was first detected in cells infected with BmNPV/A.cat at 5 hours post-infection ("p.i. ") (FIG. 3A), while in cells infected with BmNPV/P26.cat, activity above background was not observed until the 20 hour time point (FIG. 3B). The cell extracts were then diluted appropriately to obtain quantitative CAT assays for all time points and the background values, determined by the method of Example 5 at 1–2 hours post-infection, were subtracted from each point to generate the curves shown in FIG. 3C. At early times, from 5–12 hours p.i., the actin promoter was transcriptionally active resulting in significant CAT activity above background level, while no activity could be detected from the polyhedron promoter. CAT activity derived from the polyhedron promoter was detected at 20 hours p.i. At 20 hours p.i, the actin promoter was more active than the polyhedron promoter, while at 30 hours p.i. CAT activity from the two promoters was roughly equal. Finally, after 30 hours p.i. expression from the polyhedron promoter was higher than that from the actin promoter (by a factor of 3 at 50 hours p.i., the last point of the time course). Therefore, in Bm5 cells the actin promoter was active 15 hours earlier than the polyhedron promoter. It is likely that the actin promoter is active immediately upon insertion of the viral genome into the cells.

Example 7
Expression in Infected Larvae

Fifth instar B. mori larvae were injected with recombinant virus BmNPV/A.cat or BmNPV/P26.cat by the method of Example 3 and various tissues were initially assayed for CAT activity 2 days post-infection by the method of Example 4 (FIG. 4). Tissues from three larvae were pooled for each assay. Larvae infected with either virus contained high levels of CAT activity in both the head and body wall, a lower level in the midgut, and still lower expression in the gonads. Although detectable, only very low levels of CAT activity could be seen in the silk glands.

Figure 5A:
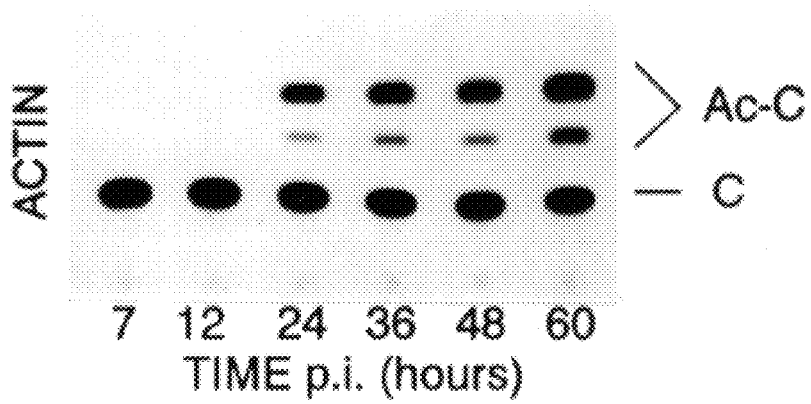

In a second set of experiments, larvae at the beginning of fifth instar were injected with the recombinant viruses BmNPV/A.cat or BmNPV/P26.cat by the method of Example 3 and body wall tissues were collected at different times post infection. The samples were then assayed for CAT activity by the method of Example 4 (FIG. 5A, B and C).

Figure 5B:
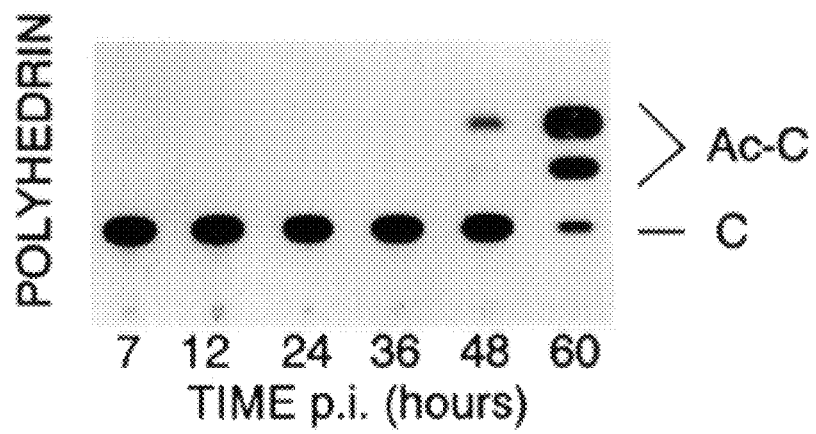
Figure 5C:
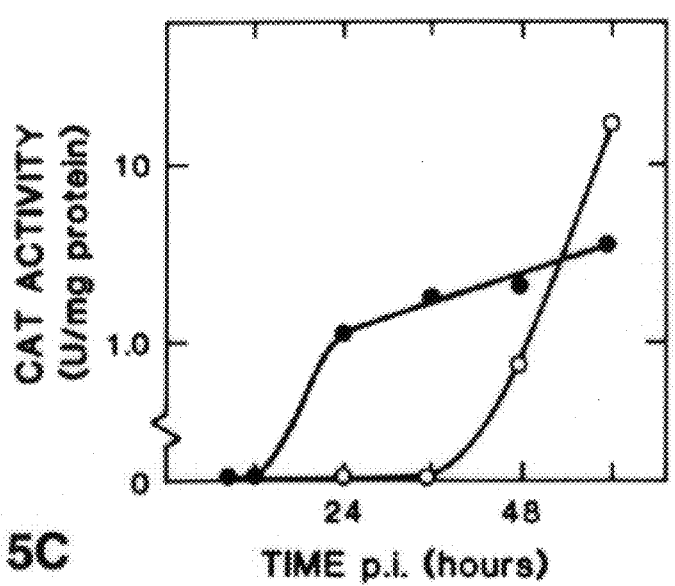

Tissues from the injected larvae contained a low level of background CAT activity at early times post infection. In larvae infected with BmNPV/A.cat, CAT activity above background was first observed in body wall tissues at 24 hours p.i. (FIG. 5A). Larvae infected with BmNPV/P26.cat did not express any CAT activity above background levels until 48 hours p.i. (FIG. 5B). A quantitative analysis of the results obtained from all time points following subtraction of the background values is shown in FIG. 5C. Even at 48 hours p.i. the actin promoter was significantly more active than the polyhedron promoter. At 60 hours p.i. the activity from the polyhedron promoter was found to be higher than that from actin but the difference in expression levels at that point was only six-fold.

Similar results were obtained from the other tissues that were examined. In all these experiments, activity from the actin promoter was seen 24 hours earlier than from the polyhedron promoter. Although the times at which CAT activity was first expressed from the two viruses in infected larvae was later than that observed in infected Bm5 cells, the general pattern of expression in vivo was similar to that observed in vitro.

Example 8
Expression in Other Lepidopteran Species

Figure 6A:
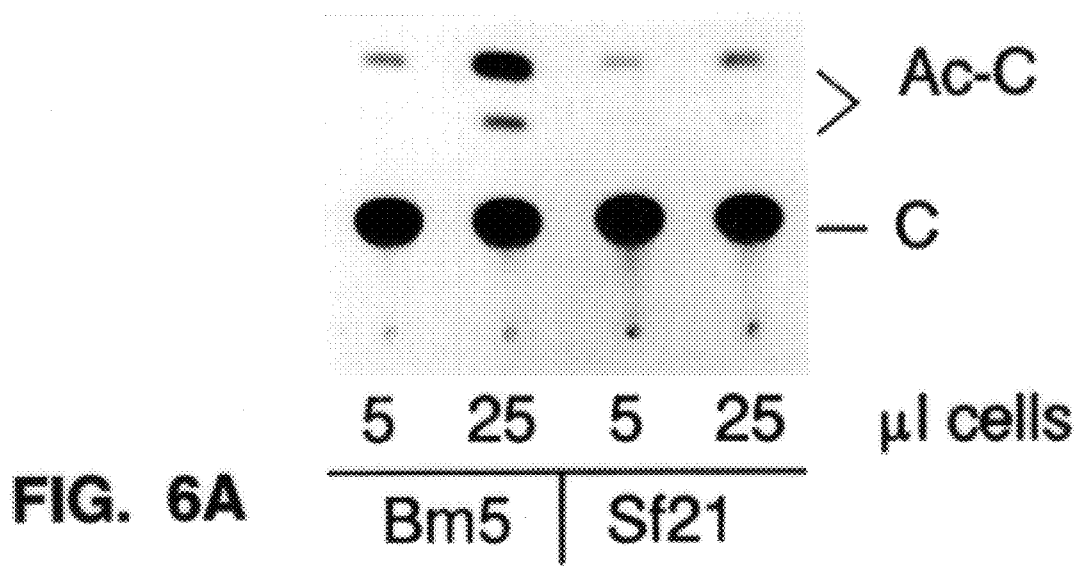

To determine the level of activity of the B. mori cytoplasmic actin promoter in cells of other insect species, plasmid pBmA.cat was transfected into tissue culture cells of both B. mori (Bm5) and Spodoptera frugiperda (Sf21) in a 24 well microliter plate. Wells were seeded with either $2 \times 10^5$ Bm5 cells or $4 \times 10^5$ Sf21 cells and the cells incubated in 200 μl transfection solution containing 5 μg/ml of pBmA.cat by the method of Example 2. Two days after transfection, cells from each well were collected, washed with PBS, lysed into 200 μl 0.25 M Tris-HCl, pH 7.8 and CAT assays were performed using either 5 μl or 25 μl of cell extracts by the method of Example 4. The Bm5 cells contained about 4 times as much CAT activity as the equivalent volume of Sf21 cells (FIG. 6A).

Figure 6B:
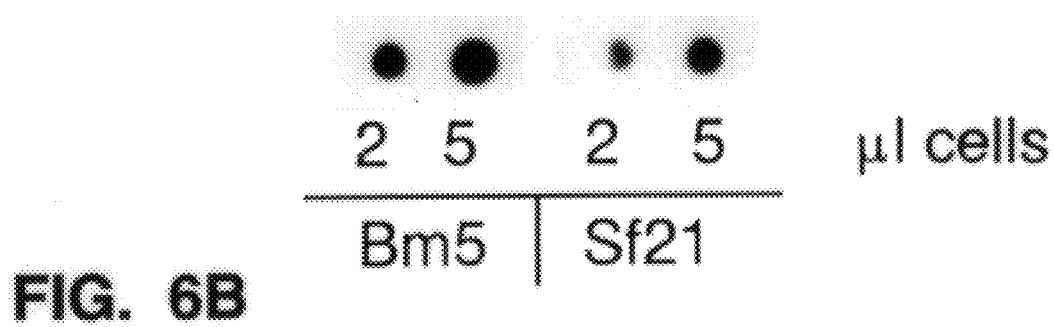

Transfected cells were collected, washed as above and suspended in 200 μl of PBS. The cell suspensions (2 μl or 5 μl ) were dot blotted onto Hybond N+ membrane (Amersham, Canada Ltd.) and treated with 0.5 M NaOH followed by 0.5 Tris-HCl, pH 7.5. Labeling of linearized pBS/SK+ DNA with α-$^{32}$P-dCTP and hybridization of this probe to the membrane was carried out at 65° C. as described by Fotaki and Iatrou (1988) J. Mol. Biol., 203:849–860. After hybridization, the membrane was washed at 65° C. in 0.1× SSC (1× SSC is 0.15 M NaCl, 0.015 M Nacitrate, pH 7.0), 0.1 % SDS and exposed to X-ray film. DNA hybridization indicated that, under the transfection conditions used, the Bm5 cells had taken up at least twice as much plasmid DNA as equivalent volumes of Sf21 cells (FIG. 6B).

These experiments, therefore, indicate that the B. mori actin promoter is active in S. frugiperda cells at levels nearly equivalent, if not equal, to those observed in B. mori cells. Similar experiments in which pBmA.cat was transfected into Cf124 tissue culture cells of the spruce budworm, Choristoneura miferana, have shown that the actin promoter is active in the latter cells at levels nearly identical to those observed in B. mori cells.

Example 9
Oral Feeding

The occluded form of BmNPV/A.cat was produced by infecting Bm5 cells simultaneously with the non-occluded forms of wild type BmNPV and BmNPV/A.cat. and collecting the resultant occlusion bodies by the following method. Tissue culture flasks (25 cm$^2$) were seeded with $2\times10^7$ Bm5 cells in 25 ml of IPL-41 medium. After 24 hours, $2\times10^6$ plaque forming units (pfu) each of wild type and recombinant extracellular virus were added to the cells. At five days post-infection (p.i.) cells and polyhedra were collected by centrifugation at 10,000×g for 5 minutes. The supernatant was removed and 5 ml of 0.4% SDS, 10 mM Tris-HCl pH 7.8 was added to the pellet from each flask. Cells were incubated for 2 hours at 22° C. with occasional agitation and polyhedra were precipitated by centrifugation at 10,000×g for 10 minutes. Polyhedra were then suspended in H$_2$O to the desired concentration, and stored at –70° C. in small aliquots.

Polyhedron derived viruses (PDV) were prepared from the polyhedra by suspending $1.2\times10^6$ polyhedra in 20 μl of freshly prepared 50 mM NaCl, 6 mM Na$_2$CO$_3$. After incubation at 22° C. for 1 hour with occasional agitation, the samples were spun at 12,000 rpm at 4° C. in a microcentrifuge for 1 hour to pellet PDV. These pellets were resuspended in 50 μl H$_2$O and centrifuged as before. Pellets were then suspended in 1 ml IPL-41 medium.

Cells to be infected with PDV were seeded into wells of a 6-well microtiter plate (10$^6$ cells in 1 ml medium) and 1 ml of the medium containing PDV was added. At 6 days p.i., the cells were collected and DNA isolated as previously described in Iatrou et al. (1985). DNA (2 μg) from these infected cells (a mixture of cellular and viral DNA) was digested with HinDII and separated on a 1% agarose gel. After transfer to nylon membranes, the DNA was probed with a 2.6 kb HinDII fragment of the BmNPV genome including the polyhedron gene as previously described in Example 8.

Each of the pure viruses has a distinct pattern on Southern blotting which can be used to determine the composition of a mixed population (FIG. 7). Analysis of cells infected with PDV from these "mixed" polyhedra indicated that these polyhedra contained a mixture of PDV from the wild type virus and from the recombinant virus.

*Bombyx mori* larvae were reared on a diet of fresh mulberry leaves and were infected with the virus at the beginning of the third instar. Larvae were starved for 6 hours at 25° C. and then placed at 4° C. overnight. After incubation at 22° C. for 1 hour, each larvae was given a 1 ×2 cm piece of mulberry leaf onto which a suspension of polyhedron had been spread (approx. $3\times10^4$ polyhedra). After a period of 6 hours, in which most of the infected leaf material was consumed, larvae were allowed to feed on fresh uninfected leaves. Larvae were dissected and CAT assays were performed as previously described in Example 4. Extracts from ten larvae were pooled for each assay. See FIG. 8.

CAT activity was observed at earlier times in the larvae infected with viruses containing the CAT gene under the control of the actin promoter than was observed when the larvae were infected with viruses containing the CAT gene under the control of the polyhedron promoter. In larvae orally infected with a mixture of BmNPV/A.cat and BmNPV a small amount of CAT activity could be detected in the gut at 7 hour p.i. and greater amounts at 12 and 24 hours p.i. In the body wall, significant CAT activity was present by 24 hours p.i. In larvae orally infected with a mixture of BmNPV/P26.cat and BmNPV, no CAT activity could be detected in the gut until 24 hours p.i. while in the body wall, no CAT activity had yet accumulated at that time. (FIG. 8) The time course of activity of the actin and polyhedron promoters in orally infected larvae is thus similar to that observed in larvae infected by hemocelic injection with extracellular virus.

The following examples are provided to illustrate the general applicability of the concept of utilization of recombinant baculoviruses containing cellular promoter-based recombinant expression cassettes directing early expression of heterologous genes (proteins) in infected insects.

Example 10
Early Expression of Additional Heterologous Genes under the Control of the Actin Promoter of *B. mori* in Insect Larvae Infected with Recombinant BmNPVs Recombinant BmNPVs expressing the heterologous proteins juvenile hormone esterase (BmNPV/A.jhe), enkephalin-like peptides (BmNPV/A.enk), proctolin (BmNPV/A.pro), alkaline phosphatase (BmNPV/A.aph), protamine (BmNPV/A.cpr), FMRF-like peptides (BmNPV/A.fmrf), insectotoxin TxP-I (BmNPV/A.TxP-I) and insectotoxin AaIT (BmNPV/A.AaIT) are constructed. Each of these recombinant baculoviruses incorporates a recombinant *B. mori* actin expression cassette containing a fragment of DNA encoding the corresponding heterologous protein, such that expression of the heterologous protein in insect cells infected with the recombinant baculovirus is directed by the *B. mori* actin promoter. The method described in Example 1 is employed to generate the recombinant expression cassettes described below, and the latter are used in conjunction with plasmid pBmp2s (FIG. IC) to generate the corresponding transplacement vectors as described in Example 1.1

(1) pBmA.jhe: A 3.0 kb EcoRI fragment from plasmid 3hv16 containing the sequence for Heliothis virescens juvenile hormone esterase cDNA (Hanzlik et al., 1990) is isolated by digestion of 3hv16 with EcoRI and inserted into the EcoRI site of the polylinker of plasmid pBmA (FIG. 1A).

(2) pBmA.enk: A 1.2 kb NcoI/BamHI fragment excised from plasmid 921 containing the sequence for bovine preproenkephalin cDNA (Gubler and Hoffman, 1983) is isolated by digestion of plasmid 921 with NcoI and the 1.2 kb fragment is inserted between the EcoRI and BamHI sites of the polylinker of plasmid pBmA.

(3) pBmA.pro: Two fragments of synthetic DNA encoding the amino acid sequences WPKRRRYLPTKRPEW (SEQ ID NO:3) and WPKRRYLPTKRPEW (SEQ ID NO:5), respectively, which include the amino acid sequence of the neuropeptide proctolin, RYLPT (Starrat & Brown, 1975) are separately inserted into the unique BstXI site of plasmid pBmA.enk. The nucleotide sequences of the two synthetic fragments are:

```
   1. (SEQ ID NO:2)
5'     GTGGCCAAAGAGAAGAAGATACCTCCCCACCAAGAGACCAGAGTG 3'
3' TCACCACCGGTTTCTCTTCTTCTATGGAGGGGTGGTTCTCTGGTC 5'
   2. (SEQ ID NO:4)
5'     GTGGCCAAAGAGAAGATACCTCCCCACCAAGAGACCAGAGTG 3'
3' TCACCACCGGTTTCTCTTCTATGGAGGGGTGGTTCTCTGGTC 5'
```

The sequences of the protruding 3' termini of the two synthetic fragments above allow their unidirectional insertion into the BstxI site of pBmA.enk. The resultant insertions are in-frame with the nucleotide sequences of preproenkephalin CDNA present in pBmA.enk such that translation of the mRNA synthesized under the control of the actin promoter yields fusion proteins which are longer than preproenkephalin by 15 or 14 amino acids, respectively, and contain the proctolin peptide sequence, RYLPT.

(4) pBmA.aph: A 2.4 kb EcoRI fragment from plasmid p.1.111 containing the structural gene for mouse tissue non-specific alkaline phosphastase (Hahnel and Schultz, 1989) is isolated by digestion of p1. 111 with EcoRI and the 2.4 kb fragment is ligated into the EcoRI site of the polylinker of plasmid pBmA.

(5) pBmA.fmrf: A 1.4 kb EcoRI fragment from plasmid pHS2A-3 containing the gene for Drosophila FMRFamide-like peptide precursor (Schneider and Taghert, 1990) is isolated by digestion of pH52A-3 with EcoRI and the 1.4 kb fragment is ligated into the EcoRI site of the polylinker of plasmid pBmA.

(6) pBmA.cpr: A 0.45 kb SmaI fragment from plasmid CPC4S4 containing the chicken protamine gene (Oliva and Dixon, 1989) is isolated by digestion of CPC454 with SmaI and the 0.45 kb fragment is ligated into the SmaI site of the polylinker of plasmid pBmA.

(7) pBmA.TxP-1: A 0.94 kb EcoRI fragment from plasmid pTox-34 containing the sequence for Pyemotes tritici insectotoxin TxP-1 cDNA (Tomalski and Miller, 1991) is isolated by digestion of pTox-34 with EcoRI and the 0.94 kb fragment is ligated into the EcoRI site of the polylinker of plasmid pBmA.

(8) pBmA.AaIT: A 0.3 kb BamHI fragment from plasmid pTZ-AaIT containing the sequence for Androctonus australis insectotoxin AaIT cDNA (McCutchen et al., 1991) is isolated by digestion with BamHI and the 0.3 kb fragment is ligated into the BamHI site of the polylinker of plasmid pBmA.

Transplacement vectors pBmp2s/A.jhe, pBmp2s/A.enk, pBmp2s/A.aph and pBmp2s/A.fmrf pBmp2s/A.pro, pBmp2s/A.cpr, pBmp2s/A.TxP-1 and pBmp2s/A.AaIT will be generated from the recombinant expression cassettes listed above, in conjunction with plasmid pBmp2s (FIG. 1C), as described in Example 1 for transplacement vector pBmp2s/A.cat (FIG. 1D). Non-occluded recombinant baculoviruses BmNPV/A.jhe, BmNPV/A.enk, BmNPV/A.pro, BmNPV/A.aph, BmNPV/A.fmrf, BmNPV/A.cpr, BmNPV/A.TxP-I and BmNPV/A.AaIT will be generated by co-transfection of Bm5 cells with DNA from wild- type BmNPV and each of the above transplacement vectors, purified and amplified, as described in Example 2.

Infection of insect larvae with each recombinant virus, as described in Example 3, will result in expression of the respective heterologous proteins under the control of the actin promoter of B. mori in essentially all insect tissues at an early stage of introduction, similar to that observed with BmNPV/A.cat. Assessments of timing of expression will be based on hybridizations of RNA extracted from tissues of infected larvae to $^{32}$P-labelled probes derived from the heterologous genes; polymerase chain reaction (PCR) amplification of cDNA generated form the same RNA using appropriate primers derived from the known sequences of the heterologous genes; detection of the heterologous proteins themselves using available antibodies; and, in the cases of BmNPV/A.TxP-1 and BmNPV/A.AaIT, also by monitoring the behavior of the infected larvae for paralytic symptoms. Oral infection of insect larvae with occluded forms of the same recombinant baculoviruses, generated as described in Example 9 for BmNPV/A.cat, will also result in early expression of the heterologous proteins in substantially all tissues of the infected larvae.

Example 11

B. mori Recombinant Expression Cassettes Inserted into Autographica californica Nuclear Polyhedrosis Virus In this example, transplacement vectors are created which can be used to generate recombinant Autographa californica Nuclear Polyhedrosis Viruses (AcNPVs) expressing the heterologous proteins listed in Example 10, under the control of the actin promoter of B. mori. In contrast to most nuclear polyhedrosis viruses, AcNPV has been shown to be capable of infecting productively several lepidopteran families. Plasmid pAc.RI-I (Smith et al., 1983), which contains the polyhedron gene of AcNPV together with 4.0 kb of 5' and 2.1 kb of 3' flanking sequences, is used. This plasmid is linearized with EcoRV which cleaves uniquely at a position located 40 bp upstream of the polyhedron gene, and the SstI fragments of the recombinant expression cassettes 1–8 listed in Example 10 above, which contain the heterologous genes under the control of the actin promoter of B. mori, are inserted into the EcoRV site of the plasmid pAc.RI-I by blunt-end ligation to generate transplacement vectors pAcp/A.jhe, pAcp/A.enk, pAcp/A.pro, pAcp/A.aph, pAcp/A.cpr, pAcp/A.fmrf, pAcp/A.TxP-I and pAcp/A.AaIT. Previous studies (Possee and Howard, 1987) have demonstrated that insertions of foreign DNA into this site of the genome of AcNPV leave all AcNPV functions unaffected, including that of the polyhedron gene, thus permitting the generation of recombinant AcNPV baculoviruses which are occluded into polyhedra.

For insertion of the recombination cassettes 1–8 on SstI fragments into the EcoRV site of plasmid pAc.RI-I, each plasmid containing a recombinant expression cassette as described in Example 10 is digested with SstI, the 3' protruding termini generated by SstI are removed by digestion with mung bean nuclease (New England Biolabs, Inc.), the SstI fragments containing the recombinant expression cassette are isolated by electroelution following electrophoresis in an agarose gel, and ligated into the EcoRV-digested plasmid pAc.RI-I with T4 DNA ligase, as described in Example 1.

Recombinant baculoviruses AcNPV/A.jhe, AcNPV/A.aph, AcNPV/A.enk, AcNPV/A.pro, AcNPV/A.cpr, AcNPV/A.fmrf, AcNPV/A.TxP-I and AcNPV/A.AaIT are generated and purified in Spodoptera frugiperda (Sf2l) cells using the DNA of the transplacement vectors above and DNA from wild-type AcNPV, as described in Example 2.

Infection of Trichoplusia ni, B. mori or Heliothis virescens insect larvae with such recombinant baculoviruses by the oral route is accomplished by spreading aqueous suspensions of polyhedra prepared from infected Sf21 cells onto the diet (foliage or artificial diets) of these insects and allowing the larvae to feed on the occlusion body-containing diet. In larvae infected with these recombinant AcNPVs, expression of the heterologous proteins under the control of the actin promoter of B. mori will occur in essentially all insect tissues at an early stage of introduction.

This suggests that it will be possible to utilize expression cassettes based on the principles described in this invention for constructing recombinant baculoviruses to be used for the control of a variety of lepidopteran species.

Example 12

Isolation of the Enhancer element

A 1.2 kb fragment of the BmNPV genome (51.8 m.u. to 52.7 m.u.) was cloned and sequenced (FIG. 9) SEQ ID NO:1). The 1.2 kb SspI fragment represents a portion of a larger 6.5 ClaI fragment (49.94 mu to 54.94 mu) which was isolated following digestion of the BmNPV genome with ClaI. The 6.5 kb ClaI fragment was isolated on the basis that it contains the CG30 and VP39 genes. Upon sequencing the 1.2 kb Sspl fragment was shown to contain a 559 bp sequence (boxed) similar to the hr sequences of AcNPV which have been shown to serve as origins of viral. DNA replication and in some cases enhancers of early viral genes (Guarino et al, 1980; Kool, M., et al., 1993).

Example 13

Enhancement of Activity in Transfected Insect Cells

To determine whether or not this enhancer element could be useful in increasing the activity of the actin promoter when used to drive the expression of foreign genes in recombinant baculoviruses, we tested its ability to stimulate the actin-cat gene in cells infected with BmNPV.

A series of gene constructs was generated containing this putative enhancer fragment in four different orientations relative to the *B. mori* cytoplasmic actin promoter. The 1.2 kb SspI fragment of BmNPV DNA containing the hr3 sequence (FIG. 9A) was inserted in both orientations into the Smal site of plasmid Bluescript SK+ ("pBS/SK+", Stratagene) to generate the plasmids p134 and p154. An SstI fragment from pBmA.cat (Example 1, FIG. 1B), containing the A3 cytoplasmic actin promoter of *B. mori* fused to the cat open reading frame, was inserted in both orientations into an SstI site in plasmids p134 and p154 to generate plasmids p13314, p13315, p15316, and p15317 (FIG. 10A).

The ability of this DNA fragment to enhance the actin promoter was assayed by transfecting Bm5 cells with each of the four plasmids and pBmA.cat. Bm5 cell cultures were maintained in IPL41 medium, containing 10% fetal calf serum as previously described In Example 2. Bm5 cells were transfected in 6-well microtiter plates as described in Example 2. The cells were transfected with equimolar amounts of the indicated plasmid (either pBmA.cat, p13314, p13315, p15316 or p15317) and 1.5 μg of pBS/SK+. The cells were collected for CAT assays at 2 days after transfection. The CAT assays were performed as described in Example 4 taking care to ensure that equal amounts of protein were tested in each sample.

In all four configurations tested, the presence of the BmNPV enhancer DNA fragment substantially stimulated expression of the cat gene functionally linked to the insect actin gene promoter (FIG. 10B).

Quantitation of these assays indicated that while Bm5 cells transfected with pBmA.cat (Example 1, FIG. 1B) contained 0.33 units CAT activity/mg protein, cells transfected with p13315 contained 29.5 U/mg, an 88-fold stimulation (FIG. 10B).

Plasmids pBmA.cat ("A.cat") or p13315 with pBS/SK+ were also transfected into *Spodoptera frugiperda* (Sf21) tissue culture cells by the method disclosed in Example 8. The 1.2 kb SspI fragment was able to stimulate expression from the actin-cat gene in Sf21 cells by a factor of 667 (FIG. 10B).

Example 14

Enhancement of Activity in Infected Insect Cells

To determine whether or not this enhancer element could be useful in increasing the activity of the actin promoter to drive the expression of foreign genes in recombinant baculoviruses, we tested its ability to stimulate the actin-cat gene in cells infected with BmNPV. Bm5 cells were infected with wild type BmNPV (10 pfu/cell) 4 hours prior to the transfection with the plasmids, by the method described in Example 3. The cells were then transfected with either a mixture of 1.0 μg pBmA.cat and 1.5 μg pBS/SK+ or with a mixture of 1.0 μg p13315 and 1.5 μg pBS/SK+. Cells were collected at 2 days after transfection and assayed for CAT activity by a method similar to that described in Example 4. Three replicates of each infection/transfection are shown. In FIG. 11, (A.cat) denotes the cells receiving plasmid pBmA.cat and (eA.cat) denotes the cells receiving plasmid p13315.

The presence of the 1.2 kb hr element was able to provide a 220-fold stimulation in the amount of cat gene expression from the actin promoter in cells infected with BmNPV virus (FIG. 11A).

The above results indicate that the *B. mori* cytoplasmic actin promoter activity was strongly enhanced by the presence of the 1.2 kb SspI fragment. Both the silkworm (Bm5) cells and the heterologous lepidopteran insect cells (Sf21) showed increased levels of atin activity in the absence of the BmNPV genome. In BmNPV-infected cells the level of enhancement was slightly higher. These results indicate that the 1.2 kb baculovirus fragment can enhance the expression of an insect cellular promoter.

Example 15

Confirmation that the plasmids containing the 1.2 kb fragment were not present in high copy number Because hr's have been shown to serve as origins of replication in AcNPV and can, under some conditions, allow plasmids containing these sequences to replicate in AcNPV-infected cells (Pearson et al., 1992; Kool et al., 1993) and because the 1.2 kb SspI fragment contains a sequence with homology to hr, the possibility existed that some of the increased expression from the cat gene functionally linked to the enhancer could have been due to the presence of an increased number of plasmids in the transfected cells. To test for this possibility, nuclei were isolated from the cells infected with BmNPV and transfected with the various plasmids in Example 14 and probed with labelled cat DNA.

Nuclei were isolated from the infected and transfected Bm5 cells by incubation in PBS containing 0.5% NP-40 at 0° for 10 minutes. After centrifugation at 4° for 10 minutes at 2,500 rpm in a microcentrifuge, the pellet was resuspended in PBS and recentrifuged as above. The pelleted nuclei were then suspended in PBS and counted with a hemocytometer. Nuclear suspensions were dot-blotted onto an Hybond N+ membrane (Amersham Canada Ltd.) and treated with 0.5 M NaOH followed by 0.5 M Tris-HCl pH 7.5. The number of nuclei blotted is indicated in FIG. 11B. Labelling of a 900 bp BamHI fragment from pBmA.cat with [α-⁼P] dCTP and hybridization of this probe to the membrane was carried out as described in Example 8. After hybridization, the membrane was washed as described in Example 8 and X-ray film was exposed to the membrane.

The plasmid containing the enhancer/actin-cat gene construct p13315 ("eA.cat") did not appear to be any more abundant in the Bm5 insect cells than the plasmid containing only the actin-cat gene construct pBmA.cat ("A.cat") (See FIG. 1B). Thus, the greatly increased level of CAT activity resulting from the presence of the enhancer is the result of an actual increase in gene expression, rather than simply an amplification of the number of genes present.

Example 16

Generation of recombinant baculoviruses containing the enhancer element

To directly test the strength of the enhanced actin promoter for gene expression in recombinant baculoviruses, an appropriate expression cassette will be constructed. The plasmid pBmeA (FIG. 12B) is similar to the plasmid pBmA (FIG. 12A; FIG. 1A) but additionally contains the enhancer sequence 5' of the actin promoter.

Figure 12B:
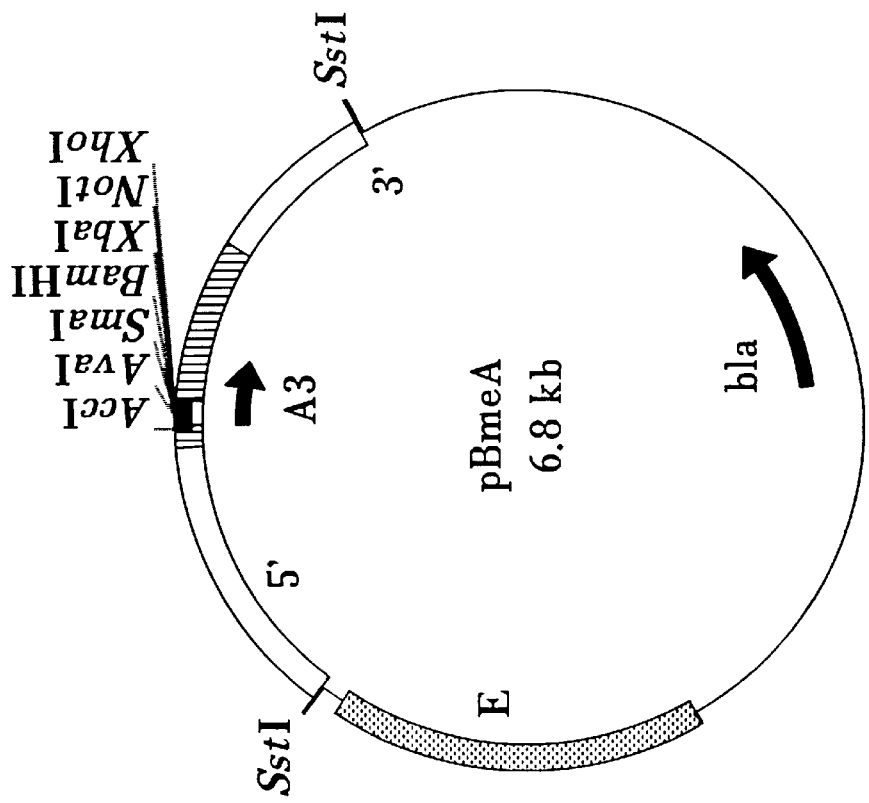
Figure 12A:
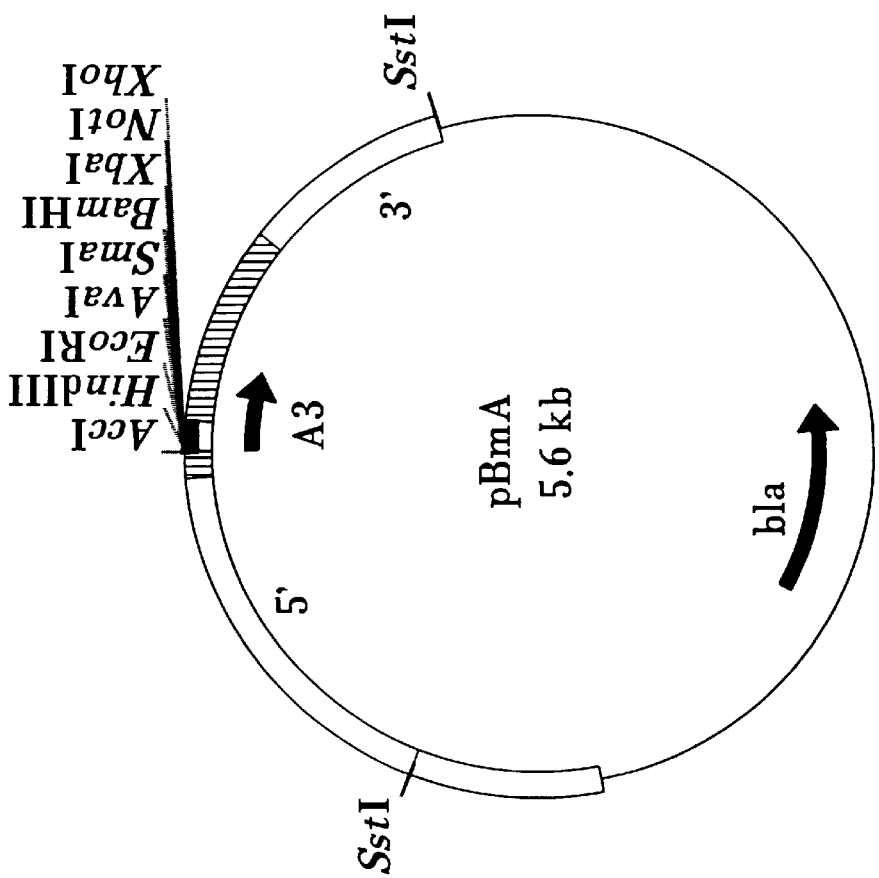

The plasmid pBmeA is constructed by:
i. digesting plasmid pBSII-SK+ (Stratagene) with XbaI and KpnI, blunt-ending and recircularizing it with DNA ligase, thus removing all polylinker sites located between XbaI and KpnI including the XbaI and KpnI sites to create plasmid pBSII-ΔSK+;
ii. linearizing pBSII-αSK+ with EagI (unique site in the polylinker of this plasmid), end-filling with Klenow polymerase and blunt-end ligating the 1.2 kb SspI enhancer fragment containing the hr3 sequence with DNA ligase to generate plasmid pBSII-ΔSK+/enhancer;
iii. subcloning into the unique SstI site of plasmid pBSII-ΔSK+/enhancer the 2.6 kb actin cassette, excised from pBmA (FIG. 12A) with SstI, to generate the enhanced expression cassette vector pBmeA (FIG. 12B).

Any open reading frame gene can then be inserted into one of the unique restriction sites present in the polylinker sequence of pBmeA to place it under the control of the enhancer-linked actin promoter.

The resultant gene fusions can then be excised as a DNA fragment with BssHII and the DNA fragment blunt-ended by end-filling with Klenow polymerase. The blunt-ended fragment can be ligated into the PmeI restriction site in transfer vector pBmp2p for the purpose of generating recombinant viruses by the method described in Example 1.

Transfer vector pBmp2p is identical to pBmp2 (Iatrou and Meidinger, 1989) except that the unique XbaI cloning site of the latter has been converted into a PmeI site through linearization with XbaI, end filling with Klenow polymerase, ligation of PmeI linkers, digestion with PmeI circularization with DNA ligase and recloning.

It is expected that recombinant viruses expressing foreign genes under the control of the enhanced actin promoter will express at an early stage of introduction (infection of insect cells) significantly higher quantities of foreign gene products than corresponding viruses utilizing the basic actin promoter.

Example 17

Cloning and use of the B. mori Transactivator Gene in Insect Tissue Culture Cells A 3.8 kb fragment of the BmNPV genome containing the IE-1 gene (Huybrechts et al. (1992) was cloned into the pBS/SK+plasmid (Stratagene) at the ClaI site to generate plasmid pBmIE1.

A 3.1 kb ClaI fragment of the AcNPV genome containing the IE-1 gene was provided by Dr. Jarvis, Texas A & M University. This 3.1 kb fragment was cloned into the pUC8 plasmid at the AccI site to generate plasmid pAcIE1.

The plasmids pBmIE1 or pAcIE1 were transfected into Bm5 insect cells by the method in Example 2. At the same time the vector pBmA.cat was also transfected into the Bm5 cells by the same method. The level of CAT expression was measured by the method in Example 4.

Figure 13A:
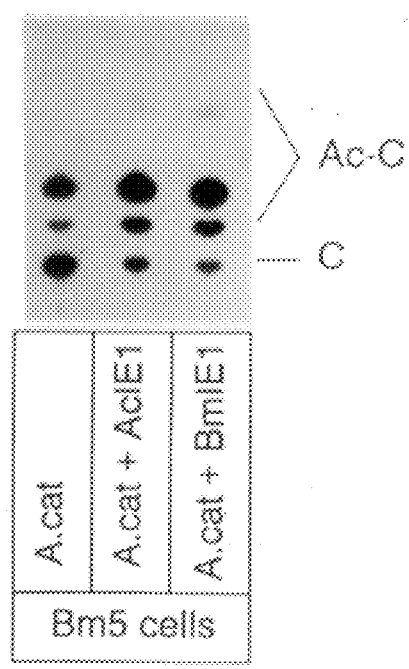

It was observed that the level of expression of the CAT protein was approximately 100 fold greater when the transactivator gene was present (FIG. 13A). From this and other experiments (See also FIG. 14) it is apparent that the IE1 product of BmNPV or AcNPV stimulates the level of expression of the cellular promoter of the recombinant cellular promoter expression cassette in trans i.e. the enhancing effect is the same irrespective of whether the gene encoding the transactivator is linked to the expression cassette or not.

Figure 13B:
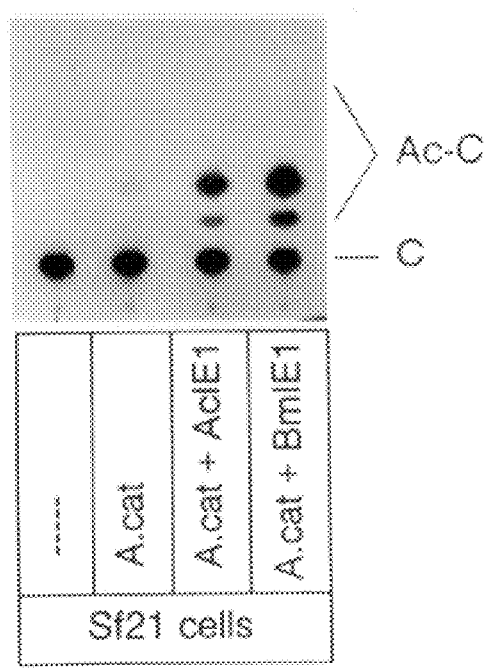

It has further been found that the gene encoding for the trans- activator and the trans-activator itself are both equally active in cell lines derived from other lepidopteran insects. (FIG. 13B) For example, it has been found that the IE-1 gene of the AcNPV (Guarino et al (1987)) could substitute for the IE-1 gene of BmNPV in both silkmoth (Bm5) and heterologous (Sf21) tissue culture cells (FIG. 13A and 13B).

By comparing cells transfected with the transactivator gene and either pBmA.cat or p13351 by the methods described in the Examples above, it has been found that the enhancing effect of the trans-activator is independent of the presence of the enhancer element.

Finally it has been found that the addition of both genetic elements to the insect cells in conjunction with the expression cassette (i.e. the enhancer linked to the expression cassette and the gene encoding for the trans-activator either linked to the cassette or supplied separately to the cells in the form of the second plasmid) results in an increase of about 2,000 to 5,000 fold in CAT protein produced from the cat gene inserted into the recombinant expression cassette under the control of the cellular promoter (FIG. 14). Similar levels of enhancement in the expression of the foreign gene product occurs also in heterologous lepidopteran cells.

REFERENCES

The following references are cited in the application and hereby incorporated by reference in their entirety.
U.S. Pat. No. 4,745,051;
U.S. Pat. No. 5,194,376;
U.S. patent application Ser. No. 07/904,408;
Bradford, 1976, *Anal. Biochem.,* 72:248–254;
Carson et al., (1988) *Virol.* 162:444–451;
Carson et al., (1991) "Transient expression of the *Autographa californica* nuclear polyhedrosis virus immediate early gene IE-N, is regulated by three viral elements", *J. Virol.* 65:945–951;
Cochran and Faulkner (1983) "Location of homologous DNA sequences interspersed at five regions in the baculovirus AcNPV genome", *J. Virol.* 45:961–970;
Fotaki and Iatrou (1988) "Identification of a transcriptionally active pseudogene in the chorion locus of the silkworm *Bombyx mori*", *J. Mol. Biol.* 203:849–860;
Gorman et al., 1982, *Mol. Cell Biol.,* 2:1044–1051
Goswami and Glazer, 1991, *Biotechniques,* 10:626–630
Grace (1967) "Establishment of a line of cells from the silkworm *Bombyx mori*" *Nature* 216:613
Granados and Lawler (1981) *J. Virol.* 108:297–308
Guarino and Dong (1991) "Expression of an enhancer-binding protein in insect cells transfected with the *Autographa californica* nuclear polyhedrosis virus IE-1 gene", *J. Virol.* 65: 3676–3680;
Guarino et al., (1986) "Complete sequence and enhancer function of the homologous DNA regions of *Autographa californica* nuclear polyhedrosis Virus", *J. Virol.* 60: 224–229;

Guarino and Summers (1986) "Interspersed homologous DNA of *Autograph californica* nuclear polyhedrosis virus enhances delayed early gene expression", *J. Virol.* 60: 215–223;

Guarino and Summers, M. D. (1987) "Nucleotide sequence and temporal expression of a baculovirus regulatory gene", *J. Virol.* 61: 2091–2099;

Gubler and Hoffman (1983) *Gene,* 25:263–269;

Hahnel and Schultz, 1989, *Clin. Chim. Acta,* 186:125–32;

Hanzlik et al., 1990, *J. Biol. Chem.,* 264:12419–12425;

Huber, J. (1986) "Use of baculoviruses in pest management programs", *In The Biology of Baculovirus* (R. R Granados and B. A. Federici, eds) CRC Press, Boca Raton, Fla.;

Huybrechts et al., (1992) "Nucleotide sequence of a trans-activating *Bombyx mori* nuclear polyhedrosis virus immediate early gene" *Biochim. Bioph. Acta* 1129:328–330;

Iatrou and Meidinger (1990) "Tissue Specific Expression of silkmoth chorion genes in vivo using *Bombyx mori* nuclear polyhedrosis virus as a transducing vector" *P.N.A.S. USA* 87:3650–3654;

Iatrou and Meidinger (1989) *"Bombyx mori* nuclear polyhedrosis virus-based vectors for expressing passenger genes in silkmoth cells under viral or cellular promoter control", *Gene* 75:59–71;

Iatrou et al. (1985) "Polyhedron gene of *Bombyx mori* nuclear polyhedrosis virus", *J. Virol* 54:436–445;

Johnson et al. (1992) "A cellular promoter-based expression cassette for generating recombinant baculoviruses directing rapid expression of passenger genes in infected insects", *Virology* 190: 815–823;

Kamita et al. (1993) "Identification and characterization of the p35 gene of *Bombyx mori* nuclear polyhedrosis virus that prevents virus-induced apoptosis", *J. Virol* 67:455–463;

Kool et al. (1993) "Location of two putative origins of DNA replication of *Autographa californica* nuclear polyhedrosis virus", *Virology* 192:94–101;

Kunkel (1985) *P.N.A.S.,* 82:488–492

Maeda et al., 1991, *Virology,* 184:777–780

Maeda and Majima (1990) "Molecular cloning and physical mapping of the genome of *Bombyx mori* nuclear polyhedrosis virus", *J. Gen. Virol.* 71: 1851–1855;

Maxam and Gilbert, 1977, *P.N.A.S.,* 74:560–564

Merryweather et al., 1990, *J. Gen. Virol.,* 71:1535–1544;

McCutchen et al., 1991, *Bio/Technology* 9:848–852;

Mitsialis et al., 1987, *P.N.A.S.,* 84:7987–7991

Mounier and Prudhomme, 1986, *Biochimie,* 68:1053–1061

Nissen and Friesen (1989) "Molecular analysis of the transcriptional regulatory region of an early baculovirus gene", *J. Virol.* 63:493–503;

Oliva and Dixon, 1989, *J. Biol. Chem.,* 264:12472–12481;

Pearson et al. (1992) "The *Autographa californica* baculovirus genome: evidence for multiple replication origins", *Science* 257: 1382–1384;

Pen et al., 1989, *Nucl. Acids Res.,* 17:451;

Possee and Howard, 1987, *Nucl. Acids Res.,* 15:10233–10248;

Schneider and Taghert, 1990, *J. Biol. Chem.,* 265:6890–6895;

Smith et al., 1983, *Mol. Cell. Biol.,* 3:2156–2165

Starrat & Brown, 1975, *Life Science,* 17:1253–1256;

Stewart et al. (1991) "Construction of an improved baculovirus insecticide containing an insect-specific toxin gene", *Nature* 352:85–88;

Tomalski and Miller (1991) "Insect paralysis by baculovirus-mediated expression of a mite gene", *Nature* 352:82–85;

Wang et al., 1991, *Gene,* 100:131–137)

Wood and Granados (1991) "Genetically engineered baculoviruses as agents for pest control", *Annu. Rev Microbiol.* 45:69–87;

---

What is claimed is:

1. A method of incapacitating insects comprising infecting an insect with an active recombinant baculovirus, such baculovirus comprising a structural gene encoding an incompatible protein functionally linked to an insect cellular promoter and an enhancer under conditions where the incompatible protein is expressed in the insect having the recombinant baculovirus present therein and the insect is incapacitated.

2. The method of claim 1 wherein the insect is infected by oral ingestion of the recombinant baculovirus.

3. The method of claim 1 wherein the insect cellular promoter comprises an insect promoter from the group consisting of ribosomal genes, histone genes, tubulin genes and actin genes.

4. The method of claim 1 wherein the incompatible protein is one selected from the group consisting of juvenile hormone esterase, enkephalin-like peptide precursor, FMRFamide-like peptide precursor, alkaline phosphate, proctolin, protamine, TxP-1 and AaIT.

5. The method of claim 1 wherein the enhancer comprises that region of the BmNPV 1.2 kb enhancer fragment which potentiates transcription from the promoter.

6. The method of claim 3 wherein the insect cellular promoter comprises the promoter sequences of the cytoplasmic actin gene of *B. mori*.

7. An enhanced expression cassette comprising a insect cellular promoter and an enhancer wherein the insect cellular promoter expresses a heterologous gene functionally linked to the promoter.

8. The expression cassette of claim 7 wherein the insect cellular promoter comprises the promoter of the cytoplasmic actin gene of *B. mori*.

9. The expression cassette of claim 7 wherein the enhancer comprises that region of the BmNPV 1.2 kb enhancer fragment which potentiates transcription from the promoter.

10. A recombinant enhanced expression cassette comprising the expression cassette of claim 7 and further comprising a heterologous structural gene functionally linked to the insect cellular promoter.

11. A transplacement fragment comprising the recombinant expression cassette of claim 10 and further comprising a portion of a baculovirus genome that can sustain insertions of non-viral DNA fragments.

12. A recombinant baculovirus comprising the recombinant expression cassette of claim 10.

13. A transplacement vector comprising the transplacement fragment of claim 11.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1189 base pairs
      (B) TYPE: nucleic acid
      (C) STRANDEDNESS: double
      (D) TOPOLOGY: linear (xi) SEQUENCE DESCRIPTION: SEQ ID NO:1:

```
AATATTAGAC AACAAAGATT TATTTTATTC ATGCCACTAC TCGGTTCCGT TTTTCAAGCT      60

AACCAGTTGT CATGCGGAAA ATGACGTCAT TATTAATGCT TTAAACGAGT TACGCAACAA     120

CGTTAAAGTG GACGCTGATT GCGATTTTTT TCAAAGACCT ATCGCACGTT TAAAACGCGT     180

ACGCTTATGT GGGCAACGGG ATTGGTTGTA GATCCGCGTA CGACGAAGAT GCGATAGTGG     240

TAAAAAAAGA AGCCGTGCCC AGTCACGTGT ACGCCAACCT GAACACGCAA TCCAACGACG     300

GCGTCAAATA CAATCGTTGG TTGCACGTTA AAAACGGCCA ATACATGGCG TGTCCTGAAG     360

AATTGTACGA TAACAACGAA TTTAAATGTA ACGTAGAATC GGATAAATTA TATTATTTGG     420

ATAATTTACA AGAAGATTCC GTTGTATAAA CATTTTATGA CGAAAACAAA TGACATCATT     480
```

```
CCTGATTATA ATAATTTTAA TCGTGCGTTA CAAGTACAAT TCTACTTGTA AAGCGAGTTT       540

AATTTGAAAA ACAAATTAGT CATTATTAAA CATGTTAACA ATCGTGTATA AAAATGACAT       600

CAGTTTAATG ATGACATCAT CTCTTGATTA TGTTTTACAC GTAGAATTCT ACTCGTAAAG       660

CCGGTTCAGT TTTGAAAAAC AAATGACATC ATCTCTTGAT TATGTTTTAC ACGTAGAATT       720

CTACTCGTAA AAGCGAGTTT AGTTTTAAAA AACAAATGAC ATCATTCAGT TTTGAAAAAC       780

AAATGACATC ATCTCTTGAT TGTGTTTTAC AAGTAGAATT CTACTCGTAA AGCGAGTTCA       840

GTTTTGAAAA ACAAATGACC CTCTCATACA ATCGTTGAAC AATTTTAATA AATAATCTTT       900

ACAAGATTCG TTTGAAGGCC TCATAAACAA TTTATATGAT TTAATATCAA TATACTTTTT       960

CAATCTAGCC TCGAATGGGC TGTTCACAAA TTACGCTTCT TCCACAATAA TTGCGTCGTA      1020

GCAAATTGCC AAATACTTGA CGCAACTAAT AACGTCTGAA TGGGTTTCAT CTTGAGCGCA      1080

CCTCCATCAT CAAAATCATA AAACGATCTA TTTGTGGGCC AAGCTGCTGT ACCGTATAAA      1140

TCGTATAATA CGACGCGGAG AAATTAATTT CTGGCACGAA CGTAATATT                  1189

(2) INFORMATION FOR SEQ ID NO:2:

(i) SEQUENCE CHARACTERISTICS:
        (A) LENGTH: 49 base pairs
        (B) TYPE: nucleic acid
        (C) STRANDEDNESS: double
        (D) TOPOLOGY: linear (xi) SEQUENCE DESCRIPTION: SEQ ID NO:2:

AGTGGTGGCC AAAGAGAAGA AGATACCTCC CCACCAAGAG ACCAGAGTG                    49

(2) INFORMATION FOR SEQ ID NO:3:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:3:

Trp Pro Lys Arg Arg Arg Tyr Leu Pro Thr Lys Arg Pro Glu Trp
1               5                   10                  15

(2) INFORMATION FOR SEQ ID NO:4:

(i) SEQUENCE CHARACTERISTICS:
        (A) LENGTH: 46 base pairs
        (B) TYPE: nucleic acid
        (C) STRANDEDNESS: double
        (D) TOPOLOGY: linear (xi) SEQUENCE DESCRIPTION: SEQ ID NO:4:

AGTGGTGGCC AAAGAGAAGA TACCTCCCCA CCAAGAGACC AGAGTG                       46

(2) INFORMATION FOR SEQ ID NO:5:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO:5:

Trp Pro Lys Arg Arg Tyr Leu Pro Thr Lys Arg Pro Glu Trp
1               5                   10
```